(12) United States Patent
Monte et al.

(10) Patent No.: US 8,367,418 B2
(45) Date of Patent: Feb. 5, 2013

(54) METHOD AND SYSTEM TO PROVIDE PERSONALIZED PHARMACEUTICAL COMPOSITIONS AND DOSAGES

(75) Inventors: Scott V. Monte, West Seneca, NY (US); Frank Bright, Williamsville, NY (US); Jerome Schentag, Amherst, NY (US)

(73) Assignee: TheraSyn Sensors, Inc., Eggertsville, NY (US)

( * ) Notice: Subject to any disclaimer, the term of this patent is extended or adjusted under 35 U.S.C. 154(b) by 114 days.

(21) Appl. No.: 12/911,497

(22) Filed: Oct. 25, 2010

(65) Prior Publication Data

US 2011/0097807 A1    Apr. 28, 2011

Related U.S. Application Data

(60) Provisional application No. 61/254,373, filed on Oct. 23, 2009.

(51) Int. Cl.
*G01N 33/66* (2006.01)
*A61K 31/70* (2006.01)

(52) U.S. Cl. ........... 436/95; 436/63; 435/14; 702/19; 514/23

(58) Field of Classification Search .......... 436/63, 436/86, 95; 435/14; 424/9.2; 702/19; 514/23
See application file for complete search history.

(56) References Cited

PUBLICATIONS

Monte et al. Journal of Diabetes Science and Technology, vol. 4, issue 2, Mar. 2010, pp. 365-381.*
Monte et al. Journal of Diabetes Science and Technology, vol. 4, issue 2, Mar. 2010, pp. 382-390.*

* cited by examiner

*Primary Examiner* — Maureen Wallenhorst
(74) *Attorney, Agent, or Firm* — Hodgson Russ LLP

(57) ABSTRACT

The invention provides a method for determining a suitable drug combination for the treatment of Type 2 diabetes by obtaining data from a Type 2 diabetes population in which all of the Type 2 diabetics are not taking any Type-2 diabetes drugs and obtaining reference levels of glucose supply and insulin demand parameters. Data from discrete samples of Type 2 diabetes populations in which all individuals are being treated with one or more Type 2 diabetes drugs at a therapeutic dose are also obtained, and the effects of the drugs on the glucose supply and insulin demand parameters are used to determine adjustment factors which represent the effect of each of the drugs at the therapeutic dosage, which are used to determined a ratio of a Glucose Supply Index (S) to an Insulin Demand Index (D). The ratio is further utilized in scoring cardiovascular risks for Type 2 diabetics and recommending therapeutic interventions.

4 Claims, 10 Drawing Sheets

Figure 6

Lookup Table

| Parameter | 0 | 1 | 2 | 3 | 4 |
|---|---|---|---|---|---|
| Age (years) | <40 | ≥40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | ≥15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease >1 artery | PCI or CABG of >1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A1C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | >160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |

Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention

Figure 7

Baseline Scoring for Patient AB:

| Parameter | 0 | 1 | 2 | 3 | 4 |
|---|---|---|---|---|---|
| Age (years) | <40 | ≥40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease >1 artery | PCI or CABG of >1 artery | MI, Ischemic Stroke |
| Body Mass Index (kg/m$^2$) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A$_1$C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary <30 minutes/wk |
| LDL-Cholesterol | <70 | 70 to 99 | 100 to 129 | 130 to 159 | ≥160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |

Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 24

Figure 8

Management Scenario 1: Insulin Glargine 47 units to be administered subcutaneously once daily at bedtime

| Parameter | 0 | 1 | 2 | 3 | 4 |
|---|---|---|---|---|---|
| Age (years) | <40 | ≥40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease >1 artery | PCI or CABG of >1 artery | MI, Ischemic Stroke |
| Body Mass Index (kg/m$^2$) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A$_1$C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | >160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |

Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 24

Figure 9

Management Scenario 2: Metformin 1,000 mg orally twice daily

| Parameter | 0 | 1 | 2 | 3 | 4 |
|---|---|---|---|---|---|
| Age (years) | <40 | ≥40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease >1 artery | PCI or CABG of >1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A₁C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | >160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |

Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 22

Figure 10

Management Scenario 3: Roux-en-Y Gastric Bypass

| Parameter | 0 | 1 | 2 | 3 | 4 |
|---|---|---|---|---|---|
| Age (years) | <40 | ≥40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease >1 artery | PCI or CABG of >1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A₁C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | >160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |

Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 15

METHOD AND SYSTEM TO PROVIDE PERSONALIZED PHARMACEUTICAL COMPOSITIONS AND DOSAGES

CROSS-REFERENCE TO RELATED APPLICATIONS

This application claims priority to U.S. Provisional application No. 61/254,373 filed on Oct. 23, 2009, the disclosure of which is incorporated herein by reference.

FIELD OF THE INVENTION

The present invention relates to management of Type 2 diabetes. In particular, the invention relates to modulating Type 2 diabetes drug therapies to improve cardiovascular outcomes.

BACKGROUND OF THE INVENTION

The most prevalent form of diabetes is Type 2 diabetes. Type 2 diabetes accounts for approximately 90-95% of all diagnosed cases of diabetes. Type 2 diabetes was previously known as non-insulin-dependent diabetes mellitus (NIDDM). Type 2 diabetes was also previously known as adult-onset diabetes. However, this form of diabetes is becoming increasingly prevalent in the growing population of overweight and clinically obese children and adults. Type 2 diabetes typically begins with insulin resistance, a disorder in which the body's cells do not respond to insulin properly, followed by a gradual loss on part of the pancreas to produce and secrete insulin in at least some patients. Type 2 diabetes is associated with a variety of factors including older age, obesity, family history of diabetes, history of gestational diabetes, impaired glucose metabolism, dietary intake of carbohydrates and glucose, low physical inactivity, and various races or ethnicities. Further conditions considered consequences of diabetes itself include hypertension and cardiovascular disease, especially atherosclerosis and vascular clotting and inflammation that may lead to ischemia of the heart tissues.

According to the American Diabetes Association, 20.6% of adults over the age of 60 have diabetes and 34.8% of all adults have either diabetes or pre-diabetes. A major goal of therapeutic treatment of diabetic patients is to delay or prevent the complications associated with chronic hyperglycemia. Cardiovascular complications are the most frequent cause of morbidity and mortality in diabetic patients. These complications include microangiopathy, retinopathy, neuropathy, nephropathy, and macroangiopathy, which is an accelerated form of atherosclerosis. Most patients with Type 2 diabetes die from cardiovascular disease, and it has only recently been demonstrated that some diabetes medicaments accelerate the development of cardiovascular disease in Type 2 diabetics, while others may prevent or slow down the rate of injury. Thus, there is an ongoing need for methods to improve Type 2 diabetes drug regimens which take into account the effects of the drugs on cardiovascular outcomes.

SUMMARY OF THE INVENTION

The invention provides a method for determining a suitable drug combination for the treatment of Type 2 diabetes by obtaining data from a Type 2 diabetes population in which all of the Type 2 diabetics are not taking any Type-2 diabetes drugs and obtaining reference levels of glucose supply parameters that include: carbohydrate exposure (CE), hepatic glucose uptake (HGU), hepatic gluconeogenesis (GNG) and insulin resistance (IR). From the data the following insulin demand parameters are also determined: peripheral glucose uptake (PGU) and peripheral insulin exposure (PIE). Data from discrete samples of Type-2 diabetes populations in which all individuals are being treated with one or more Type 2 diabetes drugs at a therapeutic dose are also obtained, and the effects of the drugs on the glucose supply and insulin demand parameters are used to determine adjustment factors which represent the effect of each of the drugs at the therapeutic dosage. The adjustment factors are used to determine a Glucose Supply Index (S) for each drug calculated as follows:

1+CE+HGU+GNG+IR, and an Insulin Demand Index (D) calculated as follows:

1+PGU+PIE.

The Glucose Supply Index and the Insulin Demand Index form a ratio which is indicative of the relationship between the effect on the glucose supply and on the insulin demand parameters for the drugs, and it is considered that an SD ratio of above 1.0 is indicative that the drug or drug combination for which the SD ratio is calculated functions on the glucose supply side of Type 2 diabetes management, while an SD ratio of below 1.0 is indicative that the drug or drug combination for which the SD ratio is calculated functions on the insulin demand supply side of Type 2 diabetes management In another embodiment, the invention also provides a method for determining modulation of cardiovascular risk for a Type 2 diabetic who is being treated with at least one drug. This embodiment comprises a) obtaining one or more physiological parameters from the Type 2 diabetic at a first time point and determining the SD ratio for the drug with that is being used to treat the Type 2 diabetic and b) assigning a first cardiovascular risk score for the individual by summing values for one or more physiological parameters that are presented in a Look-Up table. The Look-Up table is provided in FIG. 6. The SD ratio is also used to assign the first cardiovascular risk score. Steps a) and b) are repeated after a period of time, after which a second cardiovascular risk score is obtained. A lower second cardiovascular risk score compared to the first cardiovascular risk score is considered to be indicative of a reduced risk of cardiovascular disease, while a higher second cardiovascular risk score compared to the first cardiovascular risk score is considered to be indicative of an increased risk of cardiovascular disease.

If a higher second cardiovascular risk score is obtained, the invention provides for i) adjusting the dosage of the drug(s), or ii) prescribing and/or administering an additional drug(s) for; or iii) performing a surgical intervention, such as bariatric surgery.

BRIEF DESCRIPTION OF THE DRAWINGS

FIG. 6 is the Look-Up table.

FIG. 7 provides baseline risk scoring for illustrative patient AB.

FIG. 8 provides risk scoring for illustrative patient AB under insulin glargine therapy.

FIG. 9 provides risk scoring for illustrative patient AB under metformin therapy.

FIG. 10 provides risk scoring for illustrative patient AB as if Roux-en Y gastric bypass surgery had been performed.

DETAILED DESCRIPTION OF THE PREFERRED EMBODIMENTS

Figure 1:
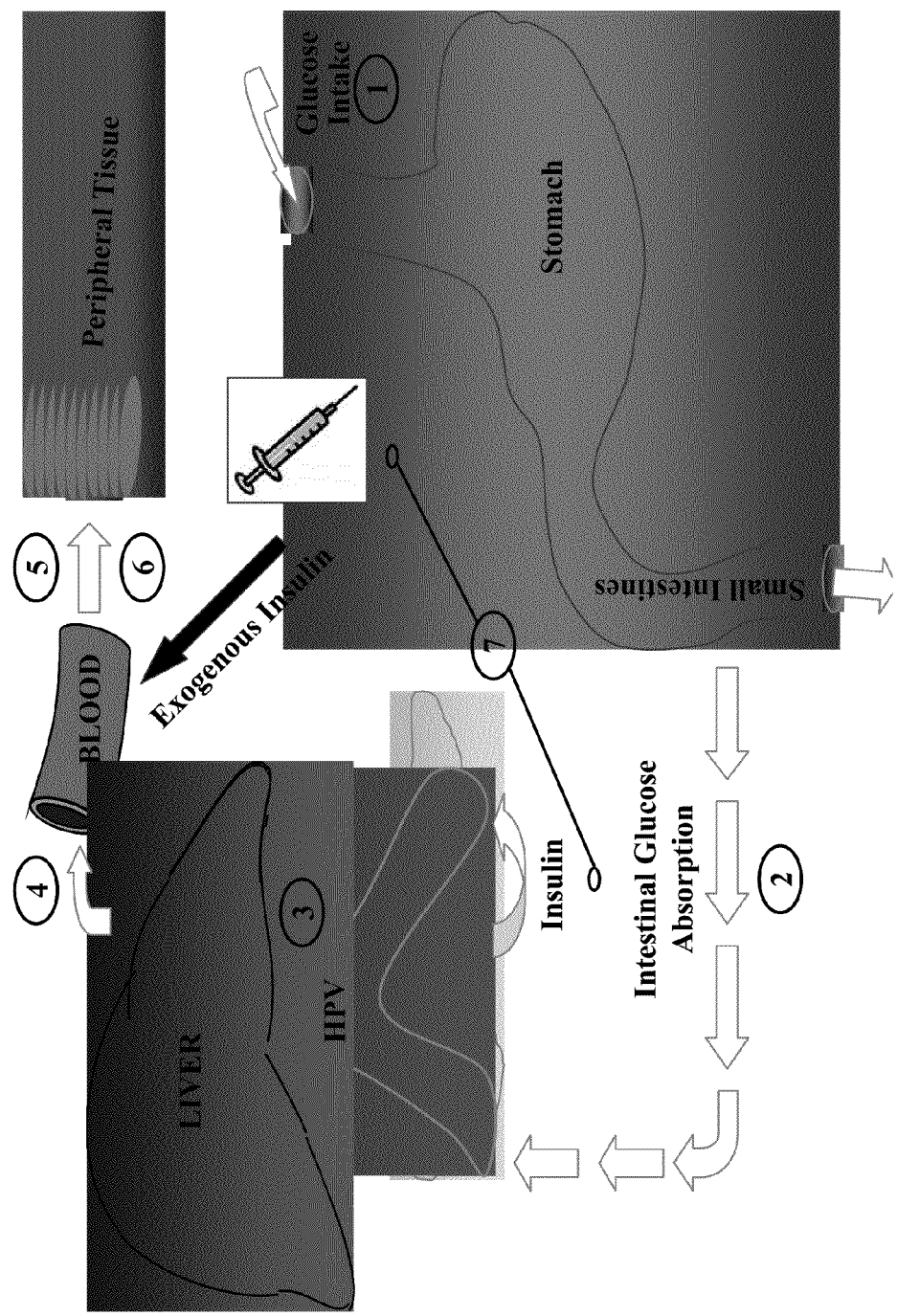
FIG. 1 is a pictorial representation of the glucose supply and insulin demand model set forth in the instant invention.

Traditional treatments of Type 2 diabetes either increase the release of insulin from the pancreas, attempt to sensitize the peripheral cells to insulin, or give additional insulin to drive more glucose into cells. We term these treatments insulin demand methods. Based on the underlying mechanisms at work in Type 2 diabetes, the insulin demand methods are less than optimal, and are likely at least partly responsible for increased cardiovascular injury in Type 2 diabetics, since cardiovascular injury is associated with abnormal increases in glucose inside the endothelial cells lining blood vessels, and the insulin demand methods all operate by increasing the glucose inside endothelial cells. In this regard, the common theme of the historical and contemporary cardiovascular outcome trials in Type 2 diabetics has been a focus on the intensive reduction of the primary biomarker, HbA1C, which is a measure of glucose in red blood cells. The American Diabetes Association (ADA)/European Association for the Study of Diabetes (EASD) consensus algorithm has been a guiding tool for the reduction of HbA1C. This algorithm advocates the initial use of metformin with subsequent addition and intensification of sulfonylurea and/or insulin therapies. Inherent to this pharmacotherapeutic approach, as well as those utilized prior to the guidelines, is an imbalance toward increased insulin exposure and increased peripheral glucose disposal, but these methods for lowering glycemia have adverse long term effects on the cardiovascular complications of diabetes patients. Thus, according to the present invention, more desirable methods for control of glycemia involve lowering the supply of glucose to endovascular cells and lowering systemic inflammation, which we term the glucose supply side of diabetes management. This methodology focuses treatments for Type 2 diabetes on the gastrointestinal tract and the liver, and moves the treatment approach away from more insulin given to Type 2 diabetics, who typically already produce excess insulin. The present invention accordingly facilitates analysis of relationships between the effect on glucose supply and insulin demand for Type 2 diabetes drugs, and furthermore provides methods for determining and modulating cardiovascular risk for Type 2 diabetics so that adjustments and/or changes in drug regimens, and/or surgical interventions can be recommended to improve cardiovascular risk by managing diabetes on the glucose supply side.

In one embodiment, the invention provides a method for determining a suitable drug combination for the treatment of Type 2 diabetes. The method comprises obtaining data from a Type 2 diabetes population, which in one embodiment is a Type 2 diabetes population in which all of the Type 2 diabetics are not taking any Type-2 diabetes drugs. The data are used to obtain reference levels of the following glucose supply parameters: carbohydrate exposure (CE), hepatic glucose uptake (HGU), hepatic gluconeogenesis (GNG) and insulin resistance (IR). The data are also used to obtain reference levels of the following insulin demand parameters: peripheral glucose uptake (PGU) and peripheral insulin exposure (PIE). The method further entails obtaining data from discrete samples of Type-2 diabetes populations in which all individuals are being treated with one or more Type 2 diabetes drugs at a therapeutic dose. The effects of the drugs on the glucose supply and insulin demand parameters are used to determine adjustment factors which represent the effect of each of the drugs at the therapeutic dosage. Adjustment factors for representative Type 2 diabetes drugs are presented in Table 1. The adjustment factors for each of the drugs on each of the glucose supply and insulin demand parameters are then used to determine a Glucose Supply Index (S) for each drug calculated as follows:

1+CE+HGU+GNG+IR, and an Insulin Demand Index (D) calculated as follows:

1+PGU+PIE.

The Glucose Supply Index and the Insulin Demand Index form a ratio (the SD ratio) which is indicative of the relationship between the effect on the glucose supply and on the insulin demand parameters for the one or more drugs. SD ratios for representative Type 2 diabetes drugs are presented in Table 1. Without intending to be bound by any particular theory, it is considered that an SD ratio of above 1.0 is indicative that the drug or drug combination for which the SD ratio is calculated functions on the glucose supply side of Type 2 diabetes management, and is therefore beneficial to the cardiovascular system for an individual receiving the drug or drug combination. It is also considered that an SD ratio of below 1.0 is indicative that the drug or drug combination for which the SD ratio is calculated functions on the insulin demand supply side of Type 2 diabetes management, and is therefore not as beneficial for an individual receiving the drug or drug combination as compared to a drug that affects the glucose supply side. Adjustment factors for pH encapsulated glucose and for Roux-en-Y gastric bypass are also shown in Table 1. It will be recognized by those in the art that the present invention is not necessarily limited to determining suitable combinations of drugs because the invention could also be used for analysis of SD ratios for single drugs.

TABLE 1

| Antidiabetic | CE inhibition | HGU uptake | GNG inhibition | IR reduction | PIE | PGU | Therapeutic Dose | SD Ratio |
| --- | --- | --- | --- | --- | --- | --- | --- | --- |
| Roux-en-Y gastric bypass | 0.75 | 0.85 | 0.75 | 0.45 | −0.35 | 0.15 | N/A | 4.75 |
| pH encapsulated glucose | 0.45 | 0.75 | 0.45 | 0.20 | −0.15 | 0.5 | N/A | 2.85 |
| Miglitol | 0.30 | 0.15 | 0.05 | 0.15 | 0.05 | 0.25 | 300 mg | 1.25 |
| Acarbose | 0.30 | 0.15 | 0.05 | 0.15 | 0.05 | 0.25 | 300 mg | 1.25 |
| Metformin | 0.15 | 0.40 | 0.35 | 0.38 | −0.10 | 0.14 | 2000 mg | 2.20 |
| Acetohexamide | 0.00 | 0.14 | 0.07 | 0.00 | 0.21 | 0.36 | 1500 mg | 0.77 |

TABLE 1-continued

| Antidiabetic | CE inhibition | HGU uptake | GNG inhibition | IR reduction | PIE | PGU | Therapeutic Dose | SD Ratio |
|---|---|---|---|---|---|---|---|---|
| Chlorpropamide | 0.00 | 0.14 | 0.07 | 0.00 | 0.21 | 0.36 | 500 mg | 0.77 |
| Tolazamide | 0.00 | 0.14 | 0.07 | 0.00 | 0.21 | 0.36 | 1000 mg | 0.77 |
| Tolbutamide | 0.00 | 0.14 | 0.07 | 0.00 | 0.21 | 0.36 | 2000 mg | 0.77 |
| Glimepiride | 0.00 | 0.18 | 0.08 | 0.00 | 0.24 | 0.39 | 8 mg | 0.77 |
| Glipizide | 0.00 | 0.18 | 0.08 | 0.00 | 0.24 | 0.39 | 10 mg | 0.77 |
| Glyburide | 0.00 | 0.14 | 0.07 | 0.00 | 0.21 | 0.36 | 10 mg | 0.77 |
| Nateglinide | 0.00 | 0.21 | 0.11 | 0.00 | 0.34 | 0.60 | 360 mg | 0.69 |
| Repaglinide | 0.00 | 0.16 | 0.07 | 0.00 | 0.20 | 0.31 | 12 mg | 0.81 |
| Pioglitazone | 0.00 | 0.40 | 0.21 | 0.35 | −0.10 | 0.59 | 45 mg | 1.32 |
| Rosiglitazone | 0.00 | 0.40 | 0.23 | 0.39 | −0.10 | 0.70 | 8 mg | 1.27 |
| Troglitazone | 0.00 | 0.40 | 0.22 | 0.35 | −0.10 | 0.67 | 600 mg | 1.25 |
| Insulin Aspart | 0.00 | 0.23 | 0.14 | 0.00 | 0.42 | 0.80 | 0.5 U/kg | 0.62 |
| Insulin Lispro | 0.00 | 0.23 | 0.14 | 0.00 | 0.42 | 0.80 | 0.5 U/kg | 0.62 |
| Insulin Regular | 0.00 | 0.21 | 0.11 | 0.00 | 0.33 | 0.64 | 0.5 U/kg | 0.67 |
| Insulin Isophane | 0.00 | 0.23 | 0.10 | 0.00 | 0.28 | 0.40 | 0.5 U/kg | 0.79 |
| Insulin Aspart Protamine | 0.00 | 0.23 | 0.10 | 0.00 | 0.28 | 0.40 | 0.5 U/kg | 0.79 |
| Insulin Lispro Protamine | 0.00 | 0.23 | 0.10 | 0.00 | 0.28 | 0.40 | 0.5 U/kg | 0.79 |
| Insulin Lente | 0.00 | 0.23 | 0.10 | 0.00 | 0.28 | 0.40 | 0.5 U/kg | 0.79 |
| Insulin Ultralente | 0.00 | 0.17 | 0.08 | 0.00 | 0.24 | 0.38 | 0.5 U/kg | 0.77 |
| Insulin Glargine | 0.00 | 0.24 | 0.10 | 0.00 | 0.30 | 0.42 | 0.5 U/kg | 0.78 |

In Table 1, under the column "CE inhibition" the adjustment factors represent decreases in carbohydrate exposure caused by the designated drug; under the column "HGU uptake" the adjustment factors represent increases in hepatic glucose uptake; under the "GNG inhibition" the adjustment factors represent decreases in hepatic gluconeogenesis; under the column "IR reduction" the adjustment factors represent decreases in insulin resistance; under the column "PIE" the adjustment factors represent increases in peripheral insulin exposure; and under the column "PGU" the adjustment factors represent increases in peripheral glucose uptake.

In certain embodiments, an SD ratio of greater than 1.1, 1.2, 1.25, 1.3, 1.35, 1.4, 1.45 or 1.5, including all integers to the second decimal place there between, or higher, is indicative that the drug or drug combination for which the SD ratio is calculated functions on the glucose supply side of Type 2 diabetes management, and is therefore beneficial for an individual receiving the drug or drug combination producing these values of the SD ratio.

In another embodiment, the invention provides a method for determining modulation of cardiovascular risk for a Type 2 diabetic who is being treated with at least one drug. The method comprises a) obtaining one or more physiological parameters from the Type 2 diabetic at a first time point and determining the SD ratio for the at least one drug with which the Type 2 diabetic is being treated, and b) assigning a first cardiovascular risk score for the individual by summing values for one or more physiological parameters in the Look-Up table provided in FIG. 6 and the SD ratio. Then steps a) and b) are repeated after a period of time, and from the Look-Up table a second cardiovascular risk score is obtained. A lower second cardiovascular risk score compared to the first cardiovascular risk score is considered to be indicative of a reduced risk of cardiovascular disease. A higher second cardiovascular risk score compared to the first cardiovascular risk score is considered to be indicative of an increased risk of cardiovascular disease.

If a higher second cardiovascular risk score is obtained, the invention provides for the following options: i) adjust the dosage of the drug(s) with which the Type 2 diabetic is being treated, or ii) prescribe and/or administer an additional drug(s) for the Type 2 diabetic; or iii) perform a surgical intervention, such as bariatric surgery, such as Roux-en-Y gastric bypass surgery.

The invention further comprises managing the Type 2 diabetic on the glucose supply side by prescribing and/or administering a composition comprising DPP-IV inhibitors or agents that function in a manner similar to DPP-IV inhibitors. The invention may further comprise administering to the Type 2 diabetic a composition comprising an agent that mimics gastric bypass surgery on the ileum. In one embodiment, an agent capable of mimicking the effects of gastric bypass surgery is a composition comprising pH encapsulated glucose, which formulated so as to be released at a pH of approximately 6.5 to 7.5, i.e., the pH environment of the ileum. Compositions comprising pH encapsulated glucose, as well as other encapsulated agents suitable for use in the invention are described in U.S. Pat. Nos. 5,322,697, 5,753,253, and 6,267,988, the disclosers of each of which are incorporated herein by reference. Alternatively, other supply side nutrients/agents can be similarly pH encapsulated so that the agents are released at pH values between 6.5 and 7.5 so as to target the ileum. Non-limiting examples of such agents include probiotic organisms, statins, antibiotics, and GLP-1 mimetics such as GLP-1. Further, any combination of agents and/or surgical procedures may be performed and/or recommended according to the invention.

Type 2 diabetic drugs that can be used for calculating reference, levels, SD ratios, and cardiovascular risk scores include but are not necessary limited to Metformin, Acetohexamide, Chlorpropamide, Tolazamide, Tolbutamide, Glimepiride, Glipizide, Glyburide, Nateglinide, Repaglinide, Pioglitazone, Rosiglitazone, Troglitazone, Insulin, Aspart, Insulin, Lispro, Insulin, Regular, Insulin, Isophane, Insulin, Aspart, Protamine, Insulin, Lispro, Protamine, Insulin, Lente, Insulin, Ultralente, Insulin, Glargine, and combinations, thereof. It will be recognized by those skilled in the art that, given the benefit of the present disclosure, any Type 2 diabetic drug now known or hereinafter developed can be analyzed and used in the method of the invention.

The Look-Up table presented in FIG. 6 provides physiological parameters which can be used in combination with the SD ratio to develop cardiovascular risk scores that are related to a Type 2 diabetic's therapeutic regimen. Those skilled in the art will recognize that additional physiological parameters may be included in the Look-Up table, or physiological parameters may be removed from it, but any such modified Look-Up table that includes an SD ratio will still be useful for developing cardiovascular risk scores without departing from the scope of the instant invention. In one embodiment, the Look-Up table includes at least the SD ratio and the Hemoglobin $A_1C$ level (also referred to as HbA1c level). Further, those skilled in the art will recognize that the risk scoring parameters (i.e., the 0, 1, 2, 3, and 4 values assigned to increasing severity of risk for each risk scoring parameter) are exemplary and can be modified, adjusted and/or replaced with any other alphanumeric characters or symbols, and in turn the summation of the risk scoring parameters can be designated in various ways that are intended to be encompassed within the invention.

It will also be recognized that any method for determining the physiological parameters, which are also considered to be biomarkers, can be used. For example, in one embodiment, a xerogel sensor can be used for biomarker measurement. Suitable methods of using xerogel sensors for testing, for example the breath of a Type 2 diabetic are described in U.S. Pat. Nos. 6,241,948 and 6,492,182 and 6,589,438, which are incorporated herein by reference. Determining Type 2 diabetes mellitus biomarkers for use in the invention can include testing of breath biomarkers which include but are not necessarily limited to oxygen, glucose, acetoacetate, betahydroxybutyrate, and other suitable free fatty acids and ketone bodies well known in the art; testing isoprostane and other metabolites of prostaglandins or any other analytes that are considered markers of oxidative stress; Nitrous oxides, methyl nitrous oxide metabolites; cytokines, proteins, incretins, peptides, adiponectin, C-Reactive Protein, procalcitonin, troponin, electrolytes, and other markers of the inflammatory pathways or those of cardiovascular injury.

In various embodiments, the present invention can be carried out using a system, which can include but is not necessarily limited to an input/output (I/O) device coupled to a processor; a communication system coupled to the processor; and/or a medical computer program and system coupled to the processor, the medical system configured to process medical data of a user and generate processed medical information, wherein the medical data includes one or more of anatomical data, diabetes associated biomarkers, test specimen data, biological parameters, health information of the user, wherein the processor is configured to dynamically control operations between the communication system and the medical system. The operations of the communication system may include one or more of a mobile device, wireless communication device, cellular telephone, Internet Protocol (IP) telephone, Wi-Fi telephone, server, personal digital assistant (PDA), and portable computer (PC). The communication system is configured to communicate one or more of the medical data and the processed medical information to a remote device located one or more of on the user, in a home, in an office, and at a medical treatment facility, the remote device including one or more of a processor-based device, mobile device, wireless device, server, personal digital assistant (PDA), cellular telephone, wearable device, and portable computer (PC). The system can include an analyzer coupled to xerogel-based substrates for concentration-dependent analyte detection, the analyzer including a xerogel-based sensor coupled to a processor configured to analyze the specimen and generate the processed medical information, wherein analysis of the specimen includes correlating parameters of the specimen with the medical data. The specimen may be a biological sample, which could include any fluid or tissue from a patient, wherein the processed medical information includes one or more of a chemical analysis of the specimen.

A device associated with the system can include a medicament delivery system coupled to the processor, the delivery system including at least one reservoir that contains at least one composition, the delivery system configured to administer at least one composition for use in treating the user, wherein the composition is administered under control of the processor and the processed medical information. The delivery system is configured to automatically or manually administer the composition or medicament.

The following example is given to illustrate the present invention. It should be understood that the invention is not to be limited to the specific conditions or details described in this example.

EXAMPLE 1

This Example provides a description of various embodiments of the invention that illustrate some of the methods by which data from a Type-2 diabetes population in which all of the individuals are not taking any Type-2 diabetes drugs can be analyzed to obtain reference levels of glucose supply and insulin demand parameters, as well as methods by which discrete samples of Type-2 diabetes populations in which all individuals in each sample are being treated with one Type 2 diabetes drugs at a therapeutic dose can be analyzed to identify adjustment factors for the effect of the dose, and in turn how to calculate and use SD ratios for individual drugs.

Therapeutic targets of the glucose supply (CE, 1+2; HGU, 3; GNG, 4; IR, 5) and insulin demand (PGU, 6; PIE, 7) model are presented in FIG. 1. To identify quantitative differences between antidiabetic agents on CE, HGU, GNG, IR, PGU, and PIE, multidatabase searches (Cochrane Central Register of Controlled Trials and Cochrane Register of Systematic Reviews, Embase, OVID Healthstar, OVID Journals, and PubMed) were conducted cross-referencing title and keywords for all selected antidiabetic therapies and their respective targets.

Alpha-glucosidase, biguanide, and thiazolidinedione (TZD) studies with long-term, pre-post design at maximal therapeutic doses were identified to simulate chronic administration. To maintain consistency with cardiovascular trials and accommodate known influences of hyperglycemia and hyperinsulinemia on the respective targets,[13-16] studies including patients with HbA1c in the range of 6-8% and body mass index (BMI)$\geq$30 kg/m$^2$ were preferentially selected. In the event multiple studies were available to identify the effect of an agent on a therapeutic target, the mean percent change was used. Conversely, if there was evidence that an agent would elicit a response on a given target but no mathematical representation of the difference was provided, conservative estimates consistent with the scale of other agents and the degree of glucose regulation were instituted to best represent the expected effect. Individual agents were then characterized for the 24 h percent change from baseline for CE, HGU, GNG, IR, PGU, and PIE. Carbohydrate exposure was determined as the combined effect of caloric intake and intestinal carbohydrate absorption. Hepatic glucose uptake was defined as the reported value obtained immediately following oral glucose loading. Because GNG is known to be enhanced in the fasting state and persistent throughout the prandial phase,[17,18] effect was determined during the fasting state and considered equivalent throughout the prandial phase. For studies evaluating fasting glucose and insulin concentrations, an index of IR was determined by homeostasis model assessment of insulin resistance (HOMAIR) using the following formula: Insulin (mU/liter)×Glucose (mmol)/22.5.[19] To account for known differences in secretory and uptake dynamics during the fasting and prandial phases, studies identifying the impact of therapies during the fasting state (or simulated hyperinsulinemic euglycemic clamp) and prandial phase (or oral glucose load insulin clamp) were specifically identified for changes in PGU (glucose infusion rate) and PIE (insulin concentrations) according to Equation (1):

$$PIE24/PGU24 = \frac{(\text{Fasting Change})(12) + (\text{Prandial Change})(12)}{24} \quad (1)$$

For sulfonylurea and insulin-based therapies, insulin concentration time profiles were obtained and superimposed on the baseline 24 h insulin concentration time profile of T2D patients (FIG. 2) to calculate the increase in PIE (trapezoidal rule).[20] Calculated increases in incremental and cumulative insulin exposure were correlated to known insulin dose-response effects on HGU, GNG, and PGU (FIG. 3),[18,21] according to the equation y=mx+b. Twenty-four-hour increases in HGU, PGU, and PIE and decreases in GNG were compared to baseline values and percent change calculated.

With alpha-glucosidase, biguanide, TZD, secretagogue, and insulin therapies characterized for their respective impacts on CE, HGU, GNG, IR, PIE, and PGU, identification of their effect on the glucose supply (decrease in CE, increase in HGU, decrease in GNG, decrease in IR) and insulin demand (increase in PIE, increase in PGU) dynamic was assessed according to Equation (2), which provides the SD ratio according to the invention:

$$\text{Glucose Supply}(S) / \text{Insulin Demand}(D) = \quad (2)$$
$$\frac{1 + ((CE) + (HGU) + (GNG) + (IR))}{1 + (PIE + PGU)}$$

Alpha-Glucosidase Inhibitors (Acarbose and Miglitol). The alpha-glucosidase inhibitors (1) have no significant effect on total caloric intake,[22] (2) delay and decrease carbohydrate absorption,[23-27] (3) have not been directly evaluated for HGU, (4) have negligible effect on hepatic glucose output,[28,29] (5) reduce IR,[22,30-33] (6) have variable effects on PGU,[22,28,30,34-38] and (7) reduce plasma insulin concentrations.[22,39-45] Studies meeting the review criteria for the target effects of the alpha-glucosidase inhibitors on the respective targets are summarized here. Estimates for the effect of alpha-glucosidase inhibitors on the respective targets are presented in Table 1.

Caloric Intake and Intestinal Carbohydrate Absorption Meneilly and associates evaluated the effects of acarbose on total caloric intake by means of 3-day food recall and dietician interview.[22] Acarbose was administered at an initial dose of 50-100 mg three times daily. At the conclusion of 52 weeks of acarbose therapy, there was no significant change in proportion of calories as carbohydrate (−0.7±0.8%), fat (0.9±0.8%), or protein (−0.5±0.5%), nor was there a significant change in total caloric intake (90±50 kcal). Radziuk evaluated the effect of 0, 50, and 100 mg of acarbose on the absorption of the glucose moiety of sucrose in overnight-fasted subjects receiving labeled 100 g oral sucrose load ([1-$^{14}$C]glucose) and simultaneous intravenous infusion of [3-$^3$H]glucose.[24] Acarbose increased malabsorption in a dose-dependent manner; at 50 mg there was a modest effect (6%), whereas at 100 mg it was approximately 30%, and at the highest 150 mg dose approximately 66%. These findings are supported by Sobajima, where carbohydrate malabsorption, measured by hydrogen excretion following 2-month acarbose administration (50-100 mg three times daily) was estimated to be 31.6% of baseline.[25]

Hepatic Glucose Uptake and Hepatic Gluconeogenesis No studies directly evaluate the impact of alpha-glucosidase inhibitors on HGU. However, evidence does suggest acarbose delays carbohydrate absorption[26,27] and increases glucagon-like peptide-1 secretion.[46,47] Therefore, it would be anticipated that alpha-glucosidase inhibitors would exhibit modest effects on retaining carbohydrate in the splanchnic area. Likewise, there is limited data regarding the impact of alpha-glucosidase inhibitors on hepatic GNG. Schnack evaluated the effect of long-term miglitol therapy on hepatic glucose output in poorly controlled T2D patients (HbA1c=9.9%). After eight weeks of therapy (300 mg/day), miglitol had no significant effect on hepatic glucose output versus placebo (0.37±0.15 versus 0.35±0.17 mg/kg$^{-1}$/min$^{-1}$) under euglycemic clamp conditions.[28] Sels evaluated the effects of miglitol on fasting plasma glucose (FPG) in T2D patients. Finding similar results, 200 mg of miglitol at bedtime for 1 week was not associated with a change in hepatic glucose production.[29]

Insulin Resistance In the study by Meneilly, IR was assessed at baseline and after 12 months of acarbose (HOMAIR). IR was significantly improved following acarbose treatment (6.1±0.5 versus 5.0±0.5).[22] At the same acarbose dose, Calle-Pascual observed reductions in FPG and fasting plasma insulin (FPI) and a slightly greater reduction in IR (~27%), as calculated by HOMAIR, after 16 weeks of therapy.[30] Concurrent with these results, Delgado observed an approximate 15% reduction in IR after 16 weeks of therapy at a lower therapeutic dose of acarbose (100 mg daily).[33] Contradicting the findings of the previous authors, Hanefeld as well as Fischer both found no significant alterations in IR.[38,41]

Peripheral Glucose Uptake Kinoshita evaluated the effect of acarbose 300 mg daily on glucose utilization rate (M value) (mg/kg$^{-1}$/min$^{-1}$) under euglycemic hyperinsulinemic conditions.[37,48] After allowing the HbA1c to fall to ≦8%, baseline clamp study was performed, with follow-up study at 6 months. At the conclusion of therapy, glucose utilization rate was increased (8.00±1.96 versus 9.94±2.35 mg/kg$^{-1}$/min$^{-1}$). At the same daily dose for 16 weeks, Fischer observed a nonsignificant increase in glucose disposal rate during euglycemic hyperinsulinemic clamp (3.2 versus 2.3 mg/kg$^{-1}$/min$^{-1}$).[38] In the study by Meneilly, glucose infusion rate during the final 20 min of the 2 h hyperglycemic clamp (5.4 mM above basal) was assessed at baseline and after 12 months of therapy. Glucose infusion rate increased significantly after acarbose therapy (1.68±0.19 versus 2.69±0.19 mg/kg$^{-1}$/min$^{-1}$).[22]Despite this evidence, multiple studies under similar experimental conditions do not confirm the observed increases in peripheral glucose disposal after sustained alpha-glucosidase therapy.[28,35,36,49]

Peripheral Insulin Exposure Numerous studies have identified a reduced postprandial insulin response following acarbose administration to T2D patients.[42-45] Meneilly as well as Hanefeld have both evaluated the combined fasting and postprandial effects of long-term acarbose administration.[22,41] Meneilly assessed fasting and postprandial insulin secretion at baseline and 12 months of acarbose therapy (100 mg three times daily), observing significant decreases in both increments (−13±4 and −271±159 pmol/liter, respectively).[22] Hanefeld evaluated the effect of acarbose therapy (100 mg three times daily) on the 24 h insulin concentration time profile. After 16 weeks of therapy, acarbose was not found to change the 24 h area under the curve of insulin from baseline.[41]

Biguanides (Metformin) Metformin has been shown to (1) reduce caloric intake, (2) have variable effects on intestinal carbohydrate absorption, (3) increase HGU, (4) diminish hepatic GNG, (5) reduce IR, (6) increase PGU, and (7) reduce insulin exposure. Estimates for the effect of metformin on the respective targets are presented in Table 1.

Caloric Intake and Intestinal Carbohydrate Absorption Anorexia is occasionally reported following the introduction of metformin therapy to T2D patients.[51] Lee and Morley evaluated the effect of metformin on caloric intake in patients with T2D. Patients were randomly given placebo, 850, or 1700 mg of metformin for 3 days and subsequently evaluated for caloric intake during three consecutive 10 min intake periods. Caloric intake was reduced during each eating interval in a dose-dependent manner. Total caloric intake during the 30 min period was reduced 30% and 50% at 850 and 1700 mg, respectively.[52] Despite the substantial reductions in caloric intake observed at the respective doses, it should be considered that the impact is thought to be sustained with only extremely high doses (>2 g/kg$^{-1}$/day$^{-1}$).[60,79] Animal and human studies to determine the impact of biguanides on intestinal carbohydrate absorption have yielded conflicting results.[53-59] Bailey reviewed the effects of metformin on intestinal glucose handling (absorption and metabolism) in animal and human models.[60] In vitro animal studies have demonstrated metformin to cause a concentration-dependent decrease in glucose transport at concentrations in the millimolar range.[61-64] In vivo, Wilcock and Bailey observed net glucose transfer in the serosal fluid was reduced 12% in mice at a dosage of 50 mg/kg (slightly greater than the maximum 3 g dose).[65] In a preparation of brush border vesicles isolated from rabbit intestine (5 mM metformin), Kessler observed a nominal decrease in glucose uptake.[66] In clinical studies of noninsulin-dependent diabetes mellitus patients, there is evidence to suggest that biguanides may delay the rate, but not the extent of glucose absorption.[58,67] During a 75 g oral glucose load challenge with labeled [1-$^{14}$C glucose], Jackson observed the absorption of glucose to be slightly delayed, but ultimately unaltered over the 3 h study period.[67] Metformin has also been noted to increase intestinal glucose utilization.[68,69] Penicaud administered 350 mg/kg$^{-1}$/day$^{-1}$ to obese fa/fa rats for 8 days, observing an increased glucose utilization by 39% in the jejunum.[68] During intravenous glucose tolerance test, Bailey administered metformin 250 mg/kg$^{-1}$ to normal rats, observing an increased glucose utilization by 30-60% in mucosa from different regions of the intestine.[69] Despite substantial increases in intestinal glucose utilization induced by metformin, it must be considered that evidence suggests an increased lactate exposure in the hepatic portal vein.[70] The increased exposure to lactate may yield increased glucose-lactate cycling between the splanchnic tissues and diminish the impact of intestinal metabolism on overall glycemia.[60]

Hepatic Glucose Uptake Iozzo evaluated the impact of metformin (2000 mg daily) and rosiglitazone (8 mg daily) therapy on HGU.[71] Positron-emission tomography (PET) studies in combination with [$^{18}$F]2-fluoro-2-deoxyglucose ([$^{18}$F]FDG) and the insulin clamp technique were performed before treatment and at 26 weeks to assess HGU. At 90 min of the 150 min normoglycemic hyperinsulinemic period, patients were intravenously administered [$^{18}$F]FDG and consecutive scans of the liver were obtained at 20 min. Although baseline HGU was not presented, metformin and rosiglitazone similarly and significantly increased HGU (placebo-subtracted value=+0.008±0.004 and +0.007±0.004 μmol/kg$^{-1}$/min$^{-1}$, respectively). Despite the failure of this study to define a specific increase versus baseline in HGU following an oral glucose load, the relationship identified between metformin and TZD would infer a similar impact.

Hepatic Gluconeogenesis Stumvoll evaluated the metabolic effects of metformin in T2D patients receiving metformin 2550 mg daily.[72] Prior to and at the conclusion of the 16 week treatment period, patients were fasted and assessed for the rate of plasma lactate to plasma glucose conversion (GNG). Metformin was found to reduce the rate of conversion by 37% (7.3±0.7 versus 4.6±0.6 μmol/kg$^{-1}$/min$^{-1}$). Hundal also evaluated the mechanism by which metformin reduces glucose production in patients with T2D.[73] To address known methodological limitations used in previous studies assessing GNG, two independent and complimentary methods (nuclear magnetic resonance spectroscopy and $^2$H$_2$O method) were employed to assess the impact of metformin therapy (2550 mg daily). Supporting the findings of Stumvoll and associates, the rate of hepatic GNG was reduced 36% as evaluated by the nuclear magnetic resonance method (0.59±0.03 versus 0.18±0.03 mmol/m$^{-2}$/min$^{-1}$) and 33% by the $^2$H$_2$O method (0.42±0.04 versus 0.28±0.03 mmol/m$^{-2}$/min$^{-1}$) after 3 months of treatment.

Insulin Resistance In a meta-analysis of randomized controlled trials in people at risk for T2D, metformin reduced calculated IR (HOMAIR) by 22.6%. In studies of patients with T2D and maximal therapeutic doses of metformin (Iozzo, Stumvoll, Tiikkainen, and Sharma), calculated IR was reduced 38-44%.[71,72,74,75]

Peripheral Glucose Uptake In the aforementioned analysis by Stumvoll, it was noted that the rate of plasma glucose turnover (hepatic glucose output and systemic glucose disposal) was reduced with metformin from 2.8±0.2 to 2.0±0.2 mg/kg$^{-1}$/min$^{-1}$.[72] Importantly, the reduction in plasma glucose turnover was attributed to the reduction in hepatic glucose output; systemic glucose disposal did not change.[72] Corroborating evidence that metformin does not substantially increase PGU, both Tiikkainen and Inzucchi observed nominal increases with long-term administration of metformin at therapeutic doses. Tiikkainen clamped patients at 144 mg/dl before and after 16 weeks of metformin 2000 mg daily. The glucose rate of disappearance remained unchanged (0.09±0.01 versus 0.10±0.01 mg/kg$^{-1}$/min$^{-1}$).[74] Inzucchi clamped patients at 100 mg/dl before and after 12 weeks of metformin 2000 mg daily. During the euglycemic hyperinsulinemic clamp period, glucose infusion rate was increased 13% (240 versus 272 mg/m$^{-2}$/min$^{-1}$).[78]

Peripheral Insulin Exposure Metformin was consistently found to reduce FPI concentrations (range: 10-30%). In the aforementioned studies by Iozzo and Stumvoll, FPI was reduced ~30% (63±12 to 43.0±5.0 pmol/liter) and 17% (12±5 to 10±μU/ml), respectively.[71,72] Tiikkainen observed an ~30% reduction in FPI (13 versus 9 mU/liter), and Sharma found an ~10% reduction (76.0±54.5 to 69.0±45.0 pmol/liter) following administration of metformin 2000 mg daily for 16 weeks.[74,75] Evaluating both the fasting and mealtime effects of metformin, Inzucchi found mean fasting and postprandial plasma insulin concentrations to be slightly, but not significantly reduced with metformin 2000 mg daily for 12 weeks.[78]

Thiazolidinediones (Pioglitazone, Rosiglitazone, and Troglitazone) The TZD agents (1) have no significant effect on total caloric intake, (2) have no evidence for diminished intestinal absorption, (3) increase HGU,[71,83,84] (4) diminish hepatic GNG, (5) reduce IR, (6) increase PGU, and (7) reduce insulin exposure. Studies meeting review criteria for the target effects of the TZDs are presented here. Estimates for the effect of TZDs on the respective targets are presented in Table 1.

Caloric Intake and Intestinal Carbohydrate Absorption The effect of TZDs on caloric intake has been evaluated in T2D patients treated with pioglitazone and rosiglitazone. Smith estimated subjective measures of hunger (visual analog scale) and satiety in patients treated with pioglitazone 45 mg/day.[80] At the conclusion of 24-weeks, pioglitazone demonstrated no effect on hunger and satiety. Strowig and Raskin assessed caloric intake via food records in patients administered rosiglitazone 4 mg twice daily.[81] At the conclusion of 32-weeks, mean caloric intake did not differ between treatment groups (rosiglitazone 2066.4±589.2 and 1994.9±726.5 calories/day for baseline and week 32, respectively). The effect of troglitazone on caloric intake in patients with diabetes has not been directly evaluated. However, in healthy volunteers, Cominancini evaluated the effects of troglitazone 400 mg daily.[82] Troglitazone was not associated with changes in carbohydrate or total caloric intake after 2 weeks of therapy.

Hepatic Glucose Uptake Bajaj and Kawamori have both evaluated the effect of pioglitazone on HGU.[83,84] Kawamori administered pioglitazone 30 mg daily to patients treated with either diet alone or sulfonylurea therapy. Following 12 weeks of therapy, the rate of splanchnic glucose uptake increased from 28.5±19.4% to 59.4±27.1% (p=0.010). Bajaj administered pioglitazone 45 mg once daily after a 48 h medication washout period. At 16 weeks, splanchnic glucose uptake increased from 33.0±2.8% to 46.2±5.1%.[83] As previously mentioned, Iozzo evaluated the effects of rosiglitazone on HGU, utilizing the insulin clamp technique and PET studies. After 26 weeks, rosiglitazone 4 mg twice daily significantly increased HGU versus placebo (+0.007 µmol/min$^{-1}$/kg$^{-1}$). Since the study did not present baseline data to allow for percent change calculation, rosiglitazone was considered to have similar characteristics to pioglitazone for HGU. Troglitazone has not been directly evaluated for impact on HGU and was considered comparable to pioglitazone and rosiglitazone.

Hepatic Gluconeogenesis Gastaldelli evaluated the fasting and mixed-meal effects of pioglitazone and rosiglitazone on hepatic GNG.[17,85] Pioglitazone 45 mg daily for 16 weeks reduced fasting endogenous glucose production (13.1±0.3 versus 12.0±0.6 7 µmol/min$^{-1}$/kg$^{-1}$) and GNG contribution (73.1±2.4% versus 64.4±3.1%). During the mixed meal, endogenous glucose production was again reduced (6.5±0.7 versus 5.4±0.7 µmol/min$^{-1}$/kg$^{-1}$) as was the contribution of GNG to the total rate of appearance (45.6±1.7% versus 41.3±2.6%).[17] In the second study, rosiglitazone 8 mg daily for 12 weeks reduced fasting endogenous glucose production (18.6±0.9 versus 16.3±0.6 µmol/min$^{-1}$/kg$^{-1}$) and GNG contribution (67±4% versus 59±3%). The direct effect of troglitazone on hepatic GNG has not been evaluated. However, Inzucchi evaluated the effect of troglitazone on endogenous glucose production and found no significant difference after administration of troglitazone 400 mg daily for 12 weeks.[78]

Insulin Resistance Langenfield evaluated the effect of pioglitazone on IR as determined by HOMAIR.[86] Pioglitazone at a dose of 45 mg daily for 24 weeks in T2D patients resulted in a decrease in IR from 6.15±4.05 to 3.85±1.92. Comparative analyses have identified similar effects of pioglitazone and rosiglitazone on IR. In a 12-week trial of pioglitazone 45 mg daily and rosiglitazone 4 mg twice daily, Goldberg reported a reduction from 8.2±0.3 to 5.4±0.2 and 7.8±0.4 to 4.8±0.2, respectively.[87] Under the same experimental design, Deeg observed similar reductions in IR for pioglitazone and rosiglitazone (8.3 versus 5.4 and 7.9 versus 4.7, respectively).[88] Yatagai evaluated the effects of troglitazone 400 mg daily on IR (HOMAIR). After 12 weeks, IR was reduced from 5.7±0.7 to 4.5±0.8.[89]

Peripheral Glucose Uptake Pioglitazone, rosiglitazone, and troglitazone have been shown to increase basal and incremental PGU. Bajaj observed the glucose infusion rate to be significantly greater during euglycemic insulin clamp (5.6 mmol/liter) after treatment with pioglitazone 45 mg daily for 16 weeks (6.9±0.5 versus 5.0±0.5 mg/kg$^{-1}$/min$^{-1}$).[83] Glucose infusion rate was also significantly increased during the 180-420 min period of the 75 g oral glucose load-insulin clamp (5.3±0.5 versus 2.9±0.5 mg/kg$^{-1}$/min$^{-1}$) Tiikkainen demonstrated that rosiglitazone 4 mg twice daily for 16 weeks increased glucose disposal rate (0.10±0.02 versus 0.17 mg/kg$^{-1}$/min$^{-1}$) with glycemic maintenance at ~8 mmol/liter.[74] Inzucchi found administration of troglitazone 400 mg daily for 12 weeks significantly increased glucose disposal rate (172 versus 265 mg/m$^{-2}$/min$^{-1}$) during the final hour of hyperinsulinemic-euglycemic clamp study (5.6 mmol/liter).[78]

Peripheral Insulin Exposure Gastaldelli evaluated the effect of pioglitazone 45 mg daily for 16 weeks on the metabolic and hormonal response to a mixed meal in T2D patients.[17] Fasting plasma insulin and plasma insulin during the mixed meal challenge (0-6 h) were similarly reduced versus baseline (88 versus 81 pmol/liter and 268 versus 248 pmol/liter, respectively). Miyazaki evaluated the dose-response effect of 7.5-45 mg of pioglitazone on fasting insulin secretion after 26 weeks. Fasting plasma insulin concentrations were similarly reduced (15-25%) at the respective pioglitazone doses.[90] Miyazaki and DeFronzo have reported that rosiglitazone demonstrates similar effects to pioglitazone on insulin secretion.[91] After 3 months of therapy with rosiglitazone 8 mg daily, FPI was reduced (18±1 versus 13±1 µU/ml) without change in the mean insulin concentration (37±4 versus 36±4 µU/ml) during a 2 h oral glucose tolerance test (OGTT). Pioglitazone similarly reduced FPI (15±1 versus 13±2 µU/ml) and also demonstrated no change in mean insulin concentration during a 2 h OGTT. Yatagai evaluated the effects of troglitazone 400 mg daily on FPI concentration in T2D patients.[89] After 12 weeks of therapy, FPI concentration was found to be slightly reduced (14.3±2.1 to 12.9±2.6 µU/ml). Similarly, Inzucchi evaluated the effects of troglitazone 400 mg daily for 12 weeks.[78] At the conclusion of the study, fasting and postprandial plasma insulin concentrations were reported to be slightly, but not significantly, reduced.

Secretagogues and Exogenous Insulin Secretagogues and exogenous insulin (1) have variable effects on caloric intake,[92-104] (2) have no evidence for diminished intestinal carbohydrate absorption, (3) increase HGU,[21] (4) diminish GNG,[18,21] (5) have variable effects on IR,[38,103,105-112] (6) increase PGU,[21] and (7) increase PIE.[113-122]

Caloric Intake and Intestinal Carbohydrate Absorption It has been hypothesized that increased plasma insulin concentrations increase appetite and cause undesirable weight gain.[92-95] The UKPDS and other studies in T2D patients have demonstrated that initiation of insulin is often accompanied by duration and intensity dependent weight gain (5-10%).[96-100] The potential cause of increased weight gain has been attributed to increased caloric intake secondary to hyperinsulinemia or hypoglycemic fear and also a reduction in the basal metabolic rate.[97,101,102] However, it must be considered that weight gain is not a universal finding and that modest reductions in daily caloric intake have been observed.[103,104] Moreover, insulin therapy is commonly, but not unequivocally, associated with increased caloric intake and subsequent weight gain.

Figure 2:
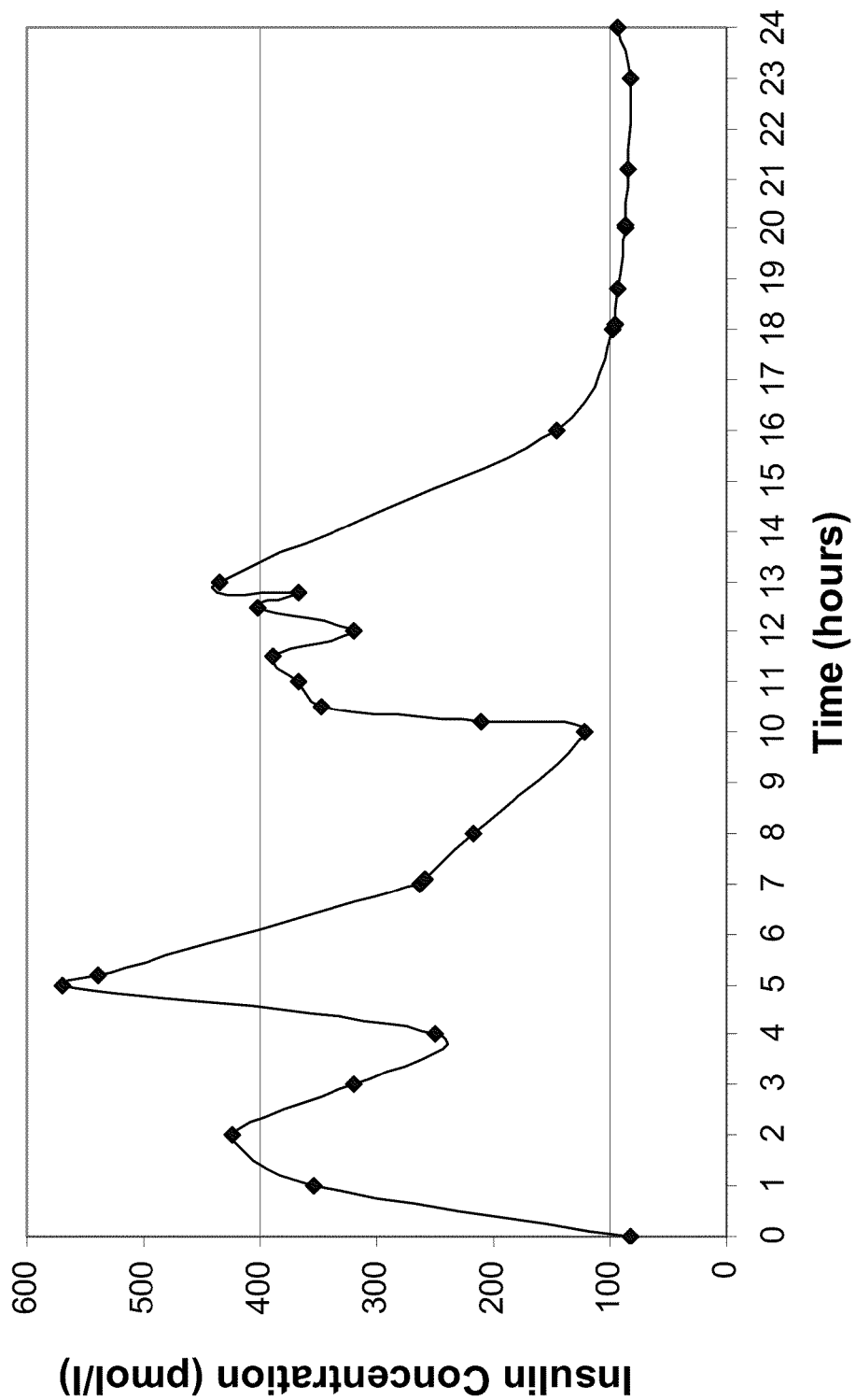
FIG. 2 is a graphical representation of a standard insulin concentration time profile for Type 2 diabetes (T2D).
Figure 3:
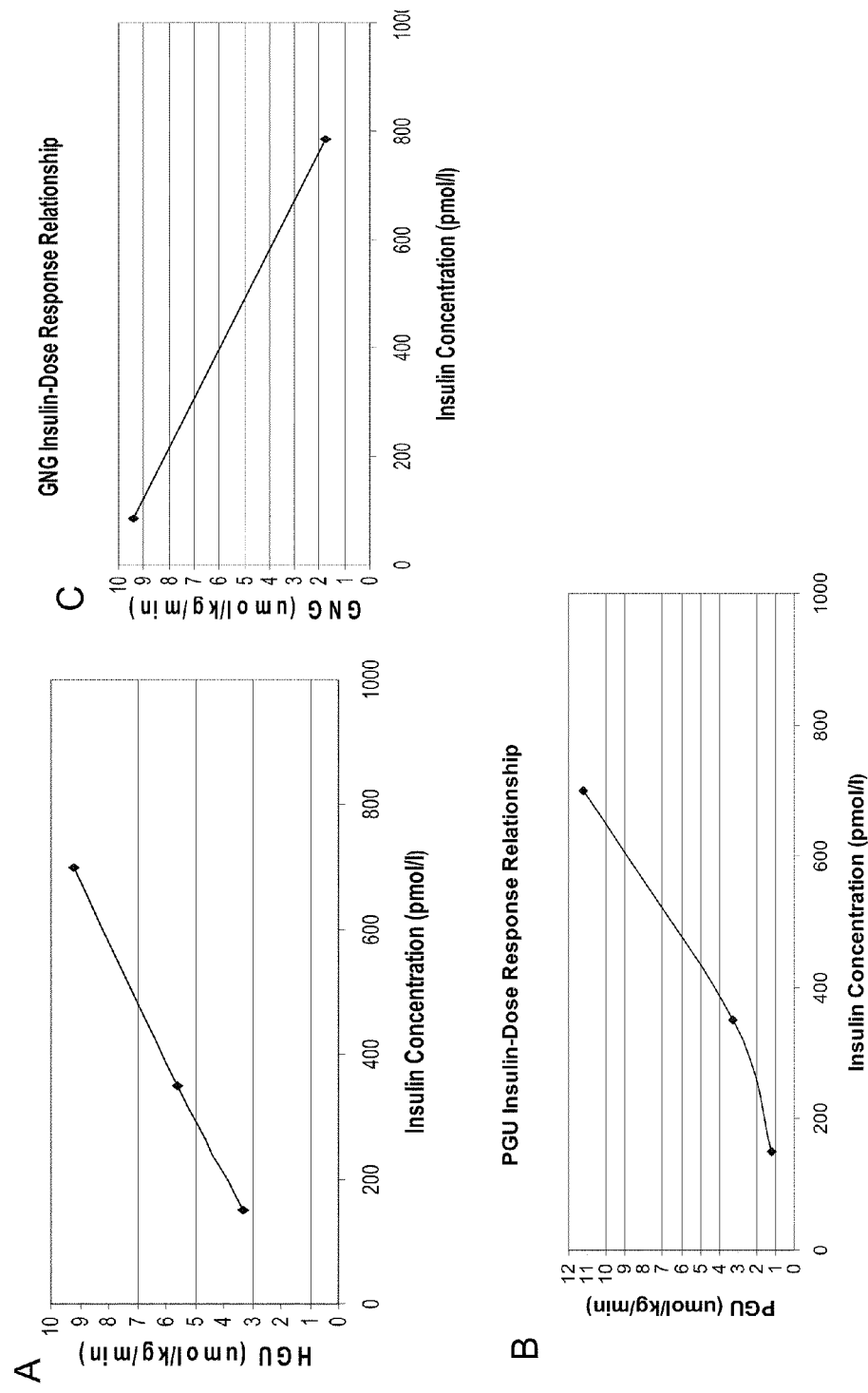
FIG. 3A is a graphical representation of HGU insulin-dose response relationship.
FIG. 3B is a graphical representation of PGU insulin-dose response relationship.
FIG. 3C is a graphical representation of GNG insulin-dose response relationship.

Standard and Insulin Concentration Time Profiles Gannon and Nuttall identified the 24 h insulin secretion profile in patients with T2D prior to initiating dietary control measures (FIG. 2). On average, patients were aged 63 years (range 51-82), with a 4-year duration of diabetes (range 1-15), BMI of 31 kg/m$^2$ (range 27-36), and a total glycosylated hemoglobin of 9.6% (range 8.6-11.2).[20]

Hepatic Glucose Uptake, Hepatic Gluconeogenesis, and Peripheral Glucose Uptake Basu evaluated the insulin dose-response curves for stimulation of splanchnic (hepatic) glucose uptake, suppression of endogenous glucose production, and PGU.[21] Patients were fed a standard 10 cal/kg meal (55% carbohydrate, 30% fat, 15% protein) and stabilized overnight at a glucose level of ~5 mmol/liter (90 mg/dl). On the subsequent morning, insulin was infused at variable rates from 0 to 180 min (~0.5 mU/kg$^{-1}$/min$^{-1}$), 181 to 300 min (~1.0 mU/kg$^{-1}$/min$^{-1}$), and 301 to 420 min (~2.0 mU/kg$^{-}$/min$^{-1}$). The insulin dose-response relationship for splanchnic glucose uptake and PGU during the final 30 min of the low- (~150 pmol/liter), medium- (~350 pmol/liter), and high- (~700 pmol/liter) dose insulin infusions are presented in FIG. 3. To most accurately quantify the hepatic contribution to glucose supply, the insulin dose-response relationship to hepatic GNG was utilized in place of total endogenous glucose production. Gastaldelli evaluated the effect of physiological hyperinsulinemia on GNG in T2D.[18] Under euglycemic clamp conditions, total rates of glucose appearance were calculated from a previously established two-compartmental model.[123] Endogenous glucose output was subsequently calculated as the difference between the rate of glucose appearance and the exogenous glucose rate. Percent contribution of GNG to the plasma glucose was calculated as the ratio of C5:$^2$H$_2$O enrichments. Under basal conditions, mean plasma insulin concentration was 12.2±1.2 µU/ml (~85 pmol/liter) and increased to 113±6 µU/ml (~780 pmol/liter) during euglycemic hyperinsulinemic clamp. Endogenous glucose output reduced from 15.2±0.4 to 7.1±0.9 and plasma C5:$^2$H$_2$O ratio declined from 0.60±0.02 to 0.25±0.02. The insulin dose-response relationship for suppression of hepatic GNG is presented in FIG. 3.

Figure 4:
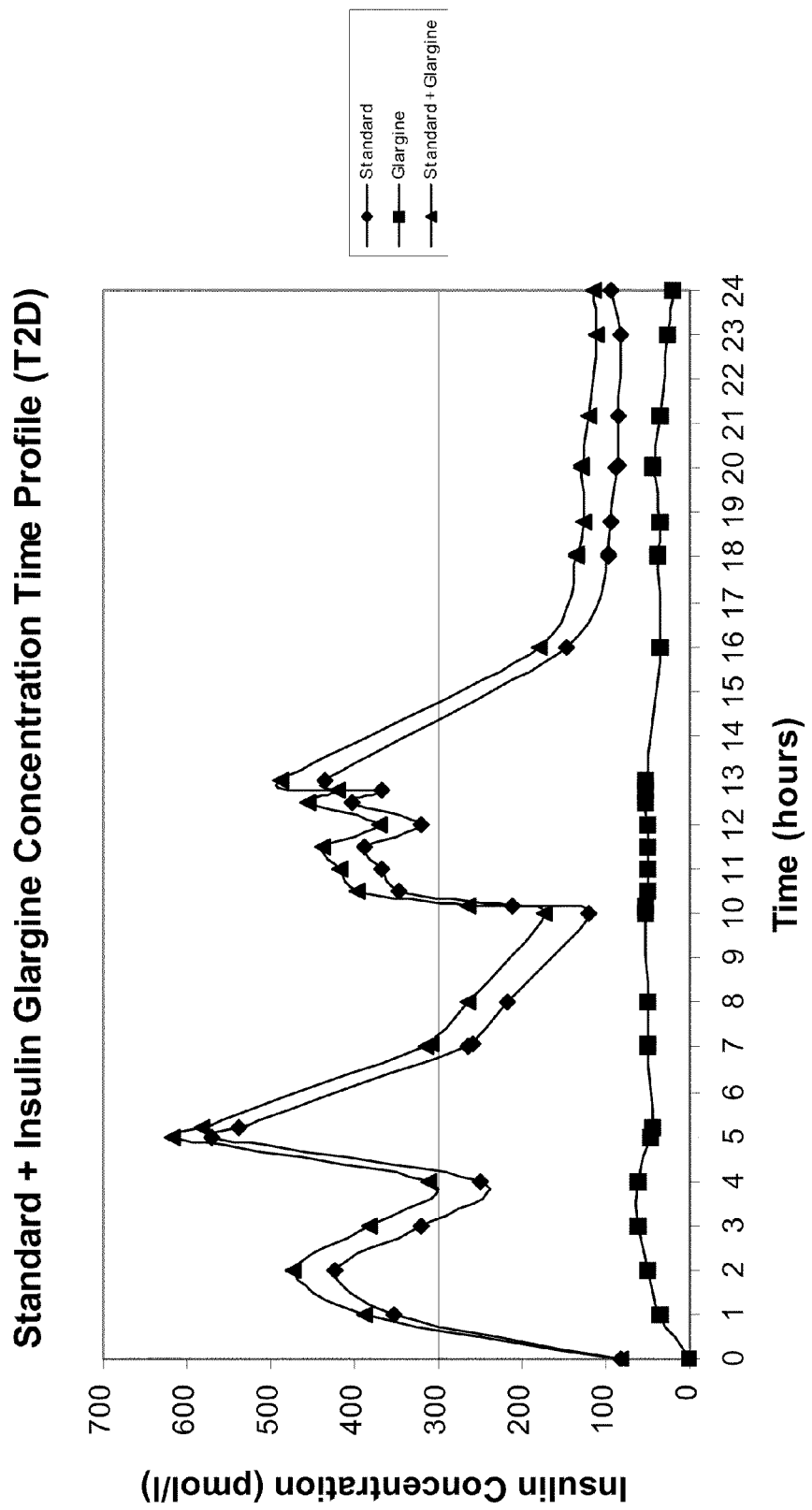
FIG. 4 is a graphical representation of standard+insulin glargine concentration time profile (T2D).

Insulin and Sulfonylurea Concentration Time Profiles Twenty-four-hour insulin concentration time curves were obtained for sulfonylurea, meglitinide, and exogenously administered insulin products.[113-122] Due to a lack of available evidence characterizing the 24 h insulin concentration profile of first generation sulfonylurea agents, comparable dose relationships were drawn with the profile for glyburide. Twenty-four-hour steady state insulin concentration time curves were superimposed on the baseline secretion profile of the standard T2D patient. As an example, the concentration time profile of insulin glargine at a dose of 0.5 U/kg is presented in FIG. 4. Using the trapezoidal rule, glargine increased PIE 30% versus baseline (5765 versus 7495 pmol/h$^{-1}$/liter$^{-1}$, respectively). Applying the superimposed 24 h insulin concentration time curve to the insulin dose-response relationships for HGU, GNG, and PGU, glargine was observed to increase HGU and PGU (24% and 42%, respectively), while decreasing GNG 10%. Hepatic glucose uptake, GNG, PGU, and PIE values for the remaining exogenously administered insulin products and sulfonylurea agents are presented in Table 1.

Insulin Resistance In 1993, Hotamisligil and colleagues identified the relationship between inflammation and metabolic conditions, such as obesity and IR, by demonstrating adipocyte expression of the pro-inflammatory cytokine tumor necrosis factor-α (TNF-α) and that expression in the adipocytes of obese animals is markedly increased.[124] Further efforts in the area of obesity have identified obesity to be a state of chronic inflammation, as indicated by increased plasma concentrations of C-reactive protein, interleukin-6 (IL-6), and plasminogen activator inhibitor-1 (PAI-1).[125-127] Dandona has characterized the anti-inflammatory effect of insulin (reduction of reactive oxygen species generation by mononuclear cells, nicotinamide adenine dinucleotide phosphate oxidase suppression, reduced intranuclear NF-κB, suppressed plasma intercellular adhesion molecule-1 and monocyte chemotactic protein-1, reduced intranuclear Egr-1, monocyte chemotactic protein-1 and PAI-1) as well as the link between IR, obesity, and diabetes.[128-130] Crook and Pickup first proposed T2D to be a chronic inflammatory condition characterized by increased concentrations of acute phase reactants (sialic acid, IL-6).[131,132] Indeed, several studies have confirmed the presence of inflammatory mediators predicts T2D.[133-139] It has been noted that the increased concentration of pro-inflammatory cytokines (i.e. TNF-α, IL-6) associated with obesity and T2D may interfere with insulin action by suppressing signal transduction. Therefore, the anti-inflammatory effects of insulin may be blunted, which in turn may promote inflammation.[130]

The extensive characterization of obesity and T2D as inflammatory conditions with blunted anti-inflammatory (and possibly pro-inflammatory) effects of insulin creates inconsistency when characterizing insulin's effect on IR. It has been argued that, by increasing weight gain, insulin therapy would exacerbate IR.[112] So too, there is conflicting evidence that insulin and sulfonylurea agents have no significant effect, or alternatively a beneficial effect, on IR as assessed by HOMAIR. Contradictory evidence in combination with known pathophysiologic evidence would indicate a net neutral effect of insulin on IR.

References for Example 1

13. DeFronzo R A, Ferrannini E, Hendler R, Wahren J, Felig P. Influence of hyperinsulinemia, hyperglycemia, and the route of glucose administration on splanchnic glucose exchange. Proc Natl Acad Sci USA. 1978; 75(10):5173-7.

14. Toschi E, Camastra S, Sironi A M, Masoni A, Gastaldelli A, Mari A, Ferrannini E, Natali A. Effect of acute hyperglycemia on insulin secretion in humans. Diabetes. 2002; 51 Suppl 1:S130-3.

15. Elahi D, Nagulesparan M, Hershcopf R J, Muller D C, Tobin J D, Blix P M, Rubenstein A H, Unger R H, Andres R. Feedback inhibition of insulin secretion by insulin: relation to the hyperinsulinemia of obesity. N Engl J Med. 1982; 306(20):1196-202.

16. Erdmann J, Mayr M, Oppel U, Sypchenko O, Wagenpfeil S, Schusdziarra V. Weight-dependent differential contribution of insulin secretion and clearance to hyperinsulinemia of obesity. Regul Pept. 2009; 152(1-3):1-7.

17. Gastaldelli A, Casolaro A, Pettiti M, Nannipieri M, Ciociaro D, Frascerra S, Buzzigoli E, Baldi S, Mari A, Ferrannini E. Effect of pioglitazone on the metabolic and hormonal response to a mixed meal in type II diabetes. Clin Pharmacol Ther. 2007; 81(2):205-12.

18. Gastaldelli A, Toschi E, Pettiti M, Frascerra S, Quiñones-Galvan A, Sironi A M, Natali A, Ferrannini E. Effect of physiological hyperinsulinemia on gluconeogenesis in nondiabetic subjects and in type 2 diabetic patients. Diabetes. 2001; 50(8):1807-12.

19. Matthews D R, Hosker J P, Rudenski A S, Naylor B A, Treacher D F, Turner R C. Homeostasis model assessment: insulin resistance and beta-cell function from fasting plasma glucose and insulin concentrations in man. Diabetologia. 1985; 28(7):412-9.
20. Gannon M C, Nuttall F Q. Effect of a high-protein, low-carbohydrate diet on blood glucose control in people with type 2 diabetes. Diabetes. 2004; 53(9):2375-82.
21. Basu R, Basu A, Johnson C M, Schwenk W F, Rizza R A. Insulin dose-response curves for stimulation of splanchnic glucose uptake and suppression of endogenous glucose production differ in nondiabetic humans and are abnormal in people with type 2 diabetes. Diabetes. 2004; 53(8):2042-50.
22. Meneilly G S, Ryan E A, Radziuk J, Lau D C, Yale J F, Morais J, Chiasson J L, Rabasa-Lhoret R, Maheux P, Tessier D, Wolever T, Josse R G, Elahi D. Effect of acarbose on insulin sensitivity in elderly patients with diabetes. Diabetes Care. 2000; 23(8):1162-7.
23. Laube H. Acarbose: an update of its therapeutic use in diabetes treatment. Clin Drug Invest. 2002; 22(3):141-56.
24. Radziuk J, Kemmer F, Morishima T, Berchtold P, Vranic M. The effects of an alpha-glucoside hydrolase inhibitor on glycemia and the absorption of sucrose in man determined using a tracer method. Diabetes. 1984; 33(3):207-13.
25. Sobajima H, Mori M, Niwa T, Muramatsu M, Sugimoto Y, Kato K, Naruse S, Kondo T, Hayakawa T. Carbohydrate malabsorption following acarbose administration. Diabet Med. 1998; 15(5):393-7.
26. Coniff R F, Shapiro J A, Robbins D, Kleinfield R, Seaton T B, Beisswenger P, McGill J B. Reduction of glycosylated hemoglobin and postprandial hyperglycemia by acarbose in patients with NIDDM. A placebo-controlled dose-comparison study. Diabetes Care. 1995; 18(6):817-24.
27. Hanefeld M, Fischer S, Schulze J, Spengler M, Wargenau M, Schollberg K, Fücker K. Therapeutic potentials of acarbose as first-line drug in NIDDM insufficiently treated with diet alone. Diabetes Care. 1991; 14(8):732-7.
28. Schnack C, Prager R J, Winkler J, Klauser R M, Schneider B G, Schernthaner G. Effects of 8-wk alpha-glucosidase inhibition on metabolic control, C-peptide secretion, hepatic glucose output, and peripheral insulin sensitivity in poorly controlled type II diabetic patients. Diabetes Care. 1989; 12(8):537-43.
29. Sels J P, Kingma P J, Wolffenbuttel B H, Menheere P P, Branolte J H, Nieuwenhuijzen Kruseman A C. Effect of miglitol (BAY m-1099) on fasting blood glucose in type 2 diabetes mellitus. Neth J Med. 1994; 44(6):198-201.
30. Calle-Pascual A, Garcia-Honduvilla J, Martin-Alvarez P J, Calle J R, Maranes J P. Influence of 16-week monotherapy with acarbose on cardiovascular risk factors in obese subjects with non-insulin-dependent diabetes mellitus: a controlled, double-blind comparison study with placebo. Diabetes Metab. 1996; 22(3):201-2.
31. Chiasson J L, Josse R G, Leiter L A, Mihic M, Nathan D M, Palmason C, Cohen R M, Wolever T M. The effect of acarbose on insulin sensitivity in subjects with impaired glucose tolerance. Diabetes Care. 1996; 19(11):1190-3.
32. Shinozaki K, Suzuki M, Ikebuchi M, Hirose J, Hara Y, Harano Y. Improvement of insulin sensitivity and dyslipidemia with a new alpha-glucosidase inhibitor, voglibose, in nondiabetic hyperinsulinemic subjects. Metabolism. 1996; 45(6):731-7.
33. Delgado H, Lehmann T, Bobbioni-Harsch E, Ybarra J, Golay A. Acarbose improves indirectly both insulin resistance and secretion in obese type 2 diabetic patients. Diabetes Metab. 2002; 28(3):195-200.
34. Laube H, Linn T, Heyen P. The effect of acarbose on insulin sensitivity and proinsulin in overweight subjects with impaired glucose tolerance. Exp Clin Endocrinol Diabetes. 1998; 106(3):231-3.
35. Reaven G M, Lardinois C K, Greenfield M S, Schwartz H C, Vreman H J. Effect of acarbose on carbohydrate and lipid metabolism in NIDDM patients poorly controlled by sulfonylureas. Diabetes Care. 1990; 13 Suppl 3: 32-6.
36. Jenney A, Proietto J, O'Dea K, Nankervis A, Traianedes K, D'Embden H. Low-dose acarbose improves glycemic control in NIDDM patients without changes in insulin sensitivity. Diabetes Care. 1993; 16(2):499-502.
37. Kinoshita T, Maeda H, Urata S, Hirao K. Effect of acarbose versus sulfonylurea therapy on insulin sensitivity: an insulin clamp study. Curr Ther Res. 1999; 61(2):97-104.
38. Fischer S, Patzak A, Rietzsch H, Schwanebeck U, Köhler C, Wildbrett J, Fuecker K, Temelkova-Kurktschiev T, Hanefeld M. Influence of treatment with acarbose or glibenclamide on insulin sensitivity in type 2 diabetic patients. Diabetes Obes Metab. 2003; 5(1):38-44.
39. Hillebrand I, Boehme K, Graefe K H, Wehling K. The effect of new alpha-glucosidase inhibitors (BAY m 1099 and BAY o 1248) on meal-stimulated increases in glucose and insulin levels in man. Klin Wochenschr. 1986; 64(8): 393-6.
40. Hillebrand I, Boehme K, Frank G, Fink H, Berchtold P. The effects of the alpha-glucosidase inhibitor BAY g 5421 (Acarbose) on meal-stimulated elevations of circulating glucose, insulin, and triglyceride levels in man. Res Exp Med (Berl). 1979; 175(1):81-6.
41. Hanefeld M, Haffner S M, Menschikowski M, Koehler C, Temelkova-Kurktschiev T, Wildbrett J, Fischer S. Different effects of acarbose and glibenclamide on proinsulin and insulin profiles in people with type 2 diabetes. Diabetes Res Clin Pract. 2002; 55(3):221-7.
42. Uttenthal L O, Ukponmwan O O, Wood S M, Ghiglione M, Ghatei M A, Trayner I M, Bloom S R. Long-term effects of intestinal alpha-glucosidase inhibition on postprandial glucose, pancreatic and gut hormone responses and fasting serum lipids in diabetics on sulphonylureas. Diabet Med. 1986; 3(2):155-60.
43. Hoffmann J, Spengler M. Efficacy of 24-week monotherapy with acarbose, glibenclamide, or placebo in NIDDM patients. The Essen Study. Diabetes Care. 1994; 17(6):561-6.
44. Inoue I, Takahashi K, Noji S, Awata T, Negishi K, Katayama S. Acarbose controls postprandial hyperproinsulinemia in non-insulin dependent diabetes mellitus. Diabetes Res Clin Pract. 1997; 36(3):143-51.
45. Rosak C, Haupt E, Walter T, Werner J. The effect of combination treatment with acarbose and glibenclamide on postprandial glucose and insulin profiles: additive blood glucose lowering effect and decreased hypoglycaemia. Diabetes Nutr Metab. 2002; 15(3):143-51.
46. Seifarth C, Bergmann J, Holst J J, Ritzel R, Schmiegel W, Nauck M A. Prolonged and enhanced secretion of glucagon-like peptide 1 (7-36 amide) after oral sucrose due to alpha-glucosidase inhibition (acarbose) in type 2 diabetic patients. Diabet Med. 1998; 15(6):485-91.
47. Gutzwiller J P. Glucagon like peptide-1 is a physiologic regulator of food intake in humans. Gastroenterology. 1997; 112:A1153.
48. DeFronzo R A, Tobin J D, Andres R. Glucose clamp technique: a method for quantifying insulin secretion and resistance. Am J Physiol. 1979; 237(3):E214-23.
49. Holman R R, Cull C A, Turner R C. A randomized double-blind trial of acarbose in type 2 diabetes shows improved glycemic control over 3 years (U.K. Prospective Diabetes Study 44). Diabetes Care. 1999; 22(6):960-4.
50. Paolisso G, Amato L, Eccellente R, Gambardella A, Tagliamonte M R, Varricchio G, Carella C, Giugliano D, D'Onofrio F. Effect of metformin on food intake in obese subjects. Eur J Clin Invest. 1998; 28(6):441-6.
51. Hermann L S. Metformin: a review of its pharmacological properties and therapeutic use. Diabete Metab. 1979; 5(3):233-45.
52. Lee A, Morley J E. Metformin decreases food consumption and induces weight loss in subjects with obesity with type II non-insulin-dependent diabetes. Obes Res. 1998; 6(1):47-53.
53. Caspary W F. Biguanides and intestinal absorptive function. Acta Hepatogastroenterol (Stuttg). 1977; 24(6):473-80.
54. Czyzyk A, Tawecki J, Sadowski J, Ponikowska I, Szczepanik Z Effect of biguanides on intestinal absorption of glucose. Diabetes. 1968; 17(8):492-8.
55. Berger W, Kunzli H. Effect of dimethylbiguanide on insulin, glucose and lactic acid contents observed in portal vein blood and peripheral venous blood in the course of intraduodenal glucose tolerance tests. Diabetologia. 1970; 6:37.
56. Gyr M, Berger W, Fridrich R, Denes A, Stadler G A. Der Einfluss von Dimethylbiguanid auf die Magenentleerung und die orale glucosetoleranz. Schw Med Wschr. 1971; 101:1876-9.
57. Adnitt P, Frayn K N. Effect of metformin on intestinal absorption and intravenous glucose tolerance in man. J Pharmacol. 1971; 2:202-4.
58. Fossati P, Fontaine P, Beuscart R, Romon M, Bourdelle-Hego M F, LePoutre-Vaast D. Escape of non insulin dependent diabetes (NIDD) to the oral hypoglycemic agents control. Rev Fr Endocrinol Clin. 1985; 26:105-16.
59. Cuber J C, Bosshard A, Vidal H, Vega F, Wiernsperger N, Rapin J R. Metabolic and drug distribution studies do not support direct inhibitory effects of metformin on intestinal glucose absorption. Diabete Metab. 1994; 20(6):532-9.
60. Bailey C J. Metformin and intestinal glucose handling. Diabetes Metab Rev. 1995; 11 Suppl 1:S23-32.
61. Caspary W F, Creutzfeldt W. Analysis of the inhibitory effect of biguanides on glucose absorption: inhibition of active sugar transport. Diabetologia. 1971; 7(5):379-85.
62. Lorch E. Inhibition of intestinal absorption and improvement of oral glucose tolerance by biguanides in the normal and in the streptozotocin-diabetic rat. Diabetologia. 1971; 7(3):195-203.
63. Coupar I M, McColl I. Glucose absorption from the rat jejunum during acute exposure to metformin and phenformin. J Pharm Pharmacol. 1974; 26(12):997-8.
64. Wilcock C, Bailey C J. Accumulation of metformin by tissues of the normal and diabetic mouse. Xenobiotica. 1994; 24(1):49-57.
65. Wilcock C, Bailey C J. Reconsideration of inhibitory effect of metformin on intestinal glucose absorption. J Pharm Pharmacol. 1991; 43(2):120-1.
66. Kessler M, Meier W, Storelli C, Semenza G. The biguanide inhibition of D-glucose transport in membrane vesicles from small intestine brush borders. Biochim Biophys Acta. 1975; 413(3):444-52.
67. Jackson R A, Hawa M I, Jaspan J B, Sim B M, Disilvio L, Featherbe D, Kurtz A B. Mechanism of metformin action in non-insulin-dependent diabetes. Diabetes. 1987; 36(5):632-40.
68. Pénicaud L, Hitier Y, Ferré P, Girard J. Hypoglycaemic effect of metformin in genetically obese (fa/fa) rats results from an increased utilization of blood glucose by intestine. Biochem J. 1989; 262(3):881-5.
69. Bailey C J, Mynett K J, Page T. Importance of the intestine as a site of metformin-stimulated glucose utilization. Br J Pharmacol. 1994; 112(2):671-5.
70. Bailey C J, Wilcock C, Day C. Effect of metformin on glucose metabolism in the splanchnic bed. Br J Pharmacol. 1992; 105(4):1009-13.
71. Iozzo P, Hallsten K, Oikonen V, Virtanen K A, Parkkola R, Kemppainen J, Solin O, Lonnqvist F, Ferrannini E, Knuuti J, Nuutila P. Effects of metformin and rosiglitazone monotherapy on insulin-mediated hepatic glucose uptake and their relation to visceral fat in type 2 diabetes. Diabetes Care. 2003; 26(7):2069-74.
72. Stumvoll M, Nurjhan N, Perriello G, Dailey G, Gerich J E. Metabolic effects of metformin in non-insulin-dependent diabetes mellitus. N Engl J Med. 1995; 333(9):550-4.
73. Hundal R S, Krssak M, Dufour S, Laurent D, Lebon V, Chandramouli V, Inzucchi S E, Schumann W C, Petersen K F, Landau B R, Shulman G I. Mechanism by which metformin reduces glucose production in type 2 diabetes. Diabetes. 2000; 49(12):2063-9.
74. Tiikkainen M, Häkkinen A M, Korsheninnikova E, Nyman T, Mäkimattila S, Yki-Järvinen H. Effects of rosiglitazone and metformin on liver fat content, hepatic insulin resistance, insulin clearance, and gene expression in adipose tissue in patients with type 2 diabetes. Diabetes. 2004; 53(8):2169-76.
75. Sharma P K, Bhansali A, Sialy R, Malhotra S, Pandhi P. Effects of pioglitazone and metformin on plasma adiponectin in newly detected type 2 diabetes mellitus. Clin Endocrinol (Oxf). 2006; 65(6):722-8.
76. Mather K J, Verma S, Anderson T J. Improved endothelial function with metformin in type 2 diabetes mellitus. J Am Coll Cardiol. 2001; 37(5):1344-50.
77. Salpeter S R, Buckley N S, Kahn J A, Salpeter E E. Meta-analysis: metformin treatment in persons at risk for diabetes mellitus. Am J Med. 2008; 121(2):149-57.e2.
78. Inzucchi S E, Maggs D G, Spollett G R, Page S L, Rife F S, Walton V, Shulman G I. Efficacy and metabolic effects of metformin and troglitazone in type II diabetes mellitus. N Engl J Med. 1998; 338(13):867-72.
79. Bailey C J, Flatt P R, Ewan C. Anorectic effect of metformin in lean and genetically obese hyperglycaemic (ob/ob) mice. Arch Int Pharmacodyn Ther. 1986; 282(2):233-9.
80. Smith S R, De Jonge L, Volaufova J, Li Y, Xie H, Bray G A. Effect of pioglitazone on body composition and energy expenditure: a randomized controlled trial. Metabolism. 2005; 54(1):24-32.
81. Strowig S M, Raskin P. The effect of rosiglitazone on overweight subjects with type 1 diabetes. Diabetes Care. 2005; 28(7):1562-7.
82. Cominacini L, Young M M, Capriati A, Garbin U, Fratta Pasini A, Campagnola M, Davoli A, Rigoni A, Contessi G B, Lo Cascio V. Troglitazone increases the resistance of low density lipoprotein to oxidation in healthy volunteers. Diabetologia. 1997; 40(10):1211-8.
83. Bajaj M, Suraamornkul S, Pratipanawatr T, Hardies L J, Pratipanawatr W, Glass L, Cersosimo E, Miyazaki Y, DeFronzo R A. Pioglitazone reduces hepatic fat content and augments splanchnic glucose uptake in patients with type 2 diabetes. Diabetes. 2003; 52(6):1364-70.
84. Kawamori R, Matsuhisa M, Kinoshita J, Mochizuki K, Niwa M, Arisaka T, Ikeda M, Kubota M, Wada M, Kanda T, Ikebuchi M, Tohdo R, Yamasaki Y. Pioglitazone enhances splanchnic glucose uptake as well as peripheral glucose uptake in non-insulin-dependent diabetes mellitus. AD-4833 Clamp-OGL Study Group. Diabetes Res Clin Pract. 1998; 41(1):35-43.

85. Gastaldelli A, Miyazaki Y, Pettiti M, Santini E, Ciociaro D, Defronzo R A, Ferrannini E. The effect of rosiglitazone on the liver: decreased gluconeogenesis in patients with type 2 diabetes. J Clin Endocrinol Metab. 2006; 91(3):806-12.

86. Langenfeld M R, Forst T, Hohberg C, Kann P, Lübben G, Konrad T, Füllert S D, Sachara C, Pfützner A. Pioglitazone decreases carotid intima-media thickness independently of glycemic control in patients with type 2 diabetes mellitus: results from a controlled randomized study. Circulation. 2005; 111(19):2525-31.

87. Goldberg R B, Kendall D M, Deeg M A, Buse J B, Zagar A J, Pinaire J A, Tan M H, Khan M A, Perez A T, Jacober S J, GLAI Study Investigators. A comparison of lipid and glycemic effects of pioglitazone and rosiglitazone in patients with type 2 diabetes and dyslipidemia. Diabetes Care. 2005; 28(7):1547-54.

88. Deeg M A, Buse J B, Goldberg R B, Kendall D M, Zagar A J, Jacober S J, Khan M A, Perez A T, Tan M H, GLAI Study Investigators. Pioglitazone and rosiglitazone have different effects on serum lipoprotein particle concentrations and sizes in patients with type 2 diabetes and dyslipidemia. Diabetes Care. 2007; 30(10):2458-64.

89. Yatagai T, Nakamura T, Nagasaka S, Kusaka I, Ishikawa S E, Yoshitaka A, Ishibashi S. Decrease in serum C-reactive protein levels by troglitazone is associated with pretreatment insulin resistance, but independent of its effect on glycemia, in type 2 diabetic subjects. Diabetes Res Clin Pract. 2004; 63(1):19-26.

90. Miyazaki Y, Matsuda M, DeFronzo R A. Dose-response effect of pioglitazone on insulin sensitivity and insulin secretion in type 2 diabetes. Diabetes Care. 2002; 25(3): 517-23.

91. Miyazaki Y, DeFronzo R A. Rosiglitazone and pioglitazone similarly improve insulin sensitivity and secretion, glucose tolerance and adipocytokines in type 2 diabetic patients. Diabetes Obes Metab. 2008; 10(12):1204-11.

92. Grossman S P. The role of glucose, insulin and glucagon in the regulation of food intake and body weight. Neurosci Biobehav Rev. 1986; 10(3):295-315.

93. Grossman M I, Stein I F Jr. Vagotomy and the hunger-producing action of insulin in man. J Appl Physiol. 1948; 1(4):263-9.

94. Thompson D A, Campbell R G. Hunger in humans induced by 2-deoxy-D-glucose: glucoprivic control of taste preference and food intake. Science. 1977; 198(4321):1065-8.

95. Westphal S A, Palumbo P J. Weight gain and management concerns in patients on insulin therapy. Insulin. 2007; 2:31-6.

96. Henry R R, Gumbiner B, Ditzler T, Wallace P, Lyon R, Glauber H S. Intensive conventional insulin therapy for type II diabetes. Metabolic effects during a 6-mo outpatient trial. Diabetes Care. 1993; 16(1):21-31.

97. Mäkimattila S, Nikkilä K, Yki-Järvinen H. Causes of weight gain during insulin therapy with and without metformin in patients with type II diabetes mellitus. Diabetologia. 1999; 42(4):406-12.

98. Lindström T, Eriksson P, Olsson A G, Arnqvist H J. Long-term improvement of glycemic control by insulin treatment in NIDDM patients with secondary failure. Diabetes Care. 1994; 17(7):719-21.

99. Yki-Järvinen H, Ryysy L, Kauppila M, Kujansuu E, Lahti J, Marjanen T, Niskanen L, Rajala S, Salo S, Seppälä P, Tulokas T, Viikari J, Taskinen M R. Effect of obesity on the response to insulin therapy in noninsulin-dependent diabetes mellitus. J Clin Endocrinol Metab. 1997; 82(12):4037-43.

100. Mudaliar S, Edelman S V. Insulin therapy in type 2 diabetes. Endocrinol Metab Clin North Am. 2001; 30(4): 935-82.

101. Rodin J, Wack J, Ferrannini E, DeFronzo R A. Effect of insulin and glucose on feeding behavior. Metabolism. 1985; 34(9):826-31.

102. Heller S. Weight gain during insulin therapy in patients with type 2 diabetes mellitus. Diabetes Res Clin Pract. 2004; 65 Suppl 1:S23-7.

103. Andrews W J, Vasquez B, Nagulesparan M, Klimes I, Foley J, Unger R, Reaven G M. Insulin therapy in obese, non-insulin-dependent diabetes induces improvements in insulin action and secretion that are maintained for two weeks after insulin withdrawal. Diabetes. 1984; 33(7):634-42.

104. Ohkubo Y, Kishikawa H, Araki E, Miyata T, Isami S, Motoyoshi S, Kojima Y, Furuyoshi N, Shichiri M. Intensive insulin therapy prevents the progression of diabetic microvascular complications in Japanese patients with non-insulin-dependent diabetes mellitus: a randomized prospective 6-year study. Diabetes Res Clin Pract. 1995; 28(2):103-17.

105. Inukai K, Watanabe M, Nakashima Y, Sawa T, Takata N, Tanaka M, Kashiwabara H, Yokota K, Suzuki M, Kurihara S, Awata T, Katayama S. Efficacy of glimepiride in Japanese type 2 diabetic subjects. Diabetes Res Clin Pract. 2005; 68(3):250-7.

106. Koshiba K, Nomura M, Nakaya Y, Ito S. Efficacy of glimepiride on insulin resistance, adipocytokines, and atherosclerosis. J Med Invest. 2006; 53(1-2):87-94.

107. Scarlett J A, Gray R S, Griffin J, Olefsky J M, Kolterman O G. Insulin treatment reverses the insulin resistance of type II diabetes mellitus. Diabetes Care. 1982; 5(4):353-63.

108. Garvey W T, Olefsky J M, Griffin J, Hamman R F, Kolterman O G. The effect of insulin treatment on insulin secretion and insulin action in type II diabetes mellitus. Diabetes. 1985; 34(3):222-34.

109. Dorkhan M, Frid A, Groop L. Differences in effects of insulin glargine or pioglitazone added to oral anti-diabetic therapy in patients with type 2 diabetes: what to add—insulin glargine or pioglitazone? Diabetes Res Clin Pract. 2008; 82(3):340-5.

110. Li J, Tian H, Li Q, Wang N, Wu T, Liu Y, Ni Z, Yu H, Liang J, Luo R, Li Y, Huang L. Improvement of insulin sensitivity and beta-cell function by nateglinide and repaglinide in type 2 diabetic patients—a randomized controlled double-blind and double-dummy multicentre clinical trial. Diabetes Obes Metab. 2007; 9(4):558-65.

111. Uwaifo G I, Ratner R E. Differential effects of oral hypoglycemic agents on glucose control and cardiovascular risk. Am J Cardiol. 2007; 99(4A):51B-67B.

112. Genuth S. Insulin use in NIDDM. Diabetes Care. 1990; 13(12):1240-64.

113. Groop L, Wåhlin-Boll E, Groop P H, Tötterman K J, Melander A, Tolppanen E M, Fyhrqvist F. Pharmacokinetics and metabolic effects of glibenclamide and glipizide in type 2 diabetics. Eur J Clin Pharmacol. 1985; 28(6):697-704.

114. Strange P, Schwartz S L, Graf R J, Polvino W, Weston I, Marbury T C, Huang W C, Goldberg R B. Pharmacokinetics, pharmacodynamics, and dose-response relationship of repaglinide in type 2 diabetes. Diabetes Technol Ther. 1999; 1(3):247-56.

115. McLeod J F. Clinical pharmacokinetics of nateglinide: a rapidly-absorbed, short-acting insulinotropic agent. Clin Pharmacokinet 2004; 43(2):97-120.
116. Plank J, Wutte A, Brunner G, Siebenhofer A, Semlitsch B, Sommer R, Hirschberger S, Pieber T R. A direct comparison of insulin aspart and insulin lispro in patients with type 1 diabetes. Diabetes Care. 2002; 25(11):2053-7.
117. Mudaliar S R, Lindberg F A, Joyce M, Beerdsen P, Strange P, Lin A, Henry R R. Insulin aspart (B28 asp-insulin): a fast-acting analog of human insulin: absorption kinetics and action profile compared with regular human insulin in healthy nondiabetic subjects. Diabetes Care. 1999; 22(9):1501-6.
118. Heinemann L, Linkeschova R, Rave K, Hompesch B, Sedlak M, Heise T. Time-action profile of the long-acting insulin analog insulin glargine (HOE901) in comparison with those of NPH insulin and placebo. Diabetes Care. 2000; 23(5):644-9.
119. Heine R J, Bilo H J, Fonk T, van der Veen E A, van der Meer J. Absorption kinetics and action profiles of mixtures of short- and intermediate-acting insulins. Diabetologia. 1984; 27(6):558-62.
120. Lepore M, Pampanelli S, Fanelli C, Porcellati F, Bartocci L, Di Vincenzo A, Cordoni C, Costa E, Brunetti P, Bolli G B. Pharmacokinetics and pharmacodynamics of subcutaneous injection of long-acting human insulin analog glargine, NPH insulin, and ultralente human insulin and continuous subcutaneous infusion of insulin lispro. Diabetes. 2000; 49(12):2142-8.
121. Rosskamp R, Wernicke-Panten K, Draeger E. Clinical profile of the novel sulphonylurea glimepiride. Diabetes Res Clin Pract. 1996; 31 Suppl:S33-42.
122. Kabadi M U, Kabadi U M. Effects of glimepiride on insulin secretion and sensitivity in patients with recently diagnosed type 2 diabetes mellitus. Clin Ther. 2004; 26(1): 63-9.
123. Natali A, Toschi E, Camastra S, Gastaldelli A, Groop L, Ferrannini E. Determinants of postabsorptive endogenous glucose output in non-diabetic subjects. European Group for the Study of Insulin Resistance (EGIR). Diabetologia. 2000; 43(10):1266-72.
124. Hotamisligil G S, Shargill N S, Spiegelman B M. Adipose expression of tumor necrosis factor-alpha: direct role in obesity-linked insulin resistance. Science. 1993; 259 (5091):87-91.
125. Yudkin J S, Stehouwer C D, Emeis J J, Coppack S W. C-reactive protein in healthy subjects: associations with obesity, insulin resistance, and endothelial dysfunction: a potential role for cytokines originating from adipose tissue? Arterioscler Thromb Vasc Biol. 1999; 19(4):972-8.
126. Mohamed-Ali V, Goodrick S, Rawesh A, Katz D R, Miles J M, Yudkin J S, Klein S, Coppack S W. Subcutaneous adipose tissue releases interleukin-6, but not tumor necrosis factor-alpha, in vivo. J Clin Endocrinol Metab. 1997; 82(12):4196-200.
127. Lundgren C H, Brown S L, Nordt T K, Sobel B E, Fujii S. Elaboration of type-1 plasminogen activator inhibitor from adipocytes. A potential pathogenetic link between obesity and cardiovascular disease. Circulation. 1996; 93(1):106-10.
128. Dandona P, Aljada A, Mohanty P, Ghanim H, Hamouda W, Assian E, Ahmad S. Insulin inhibits intranuclear nuclear factor kappaB and stimulates IkappaB in mononuclear cells in obese subjects: evidence for an anti-inflammatory effect? J Clin Endocrinol Metab. 2001; 86(7):3257-65.
129. Aljada A, Ghanim H, Mohanty P, Kapur N, Dandona P. Insulin inhibits the pro-inflammatory transcription factor early growth response gene-1 (Egr)-1 expression in mononuclear cells (MNC) and reduces plasma tissue factor (TF) and plasminogen activator inhibitor-1 (PAI-1) concentrations. J Clin Endocrinol Metab. 2002; 87(3):1419-22.
130. Dandona P, Aljada A, Bandyopadhyay A. Inflammation: the link between insulin resistance, obesity and diabetes. Trends Immunol. 2004; 25(1):4-7.
131. Crook M A, Tutt P, Pickup J C. Elevated serum sialic acid concentration in NIDDM and its relationship to blood pressure and retinopathy. Diabetes Care. 1993; 16(1):57-60.
132. Pickup J C, Mattock M B, Chusney G D, Burt D. NIDDM as a disease of the innate immune system: association of acute-phase reactants and interleukin-6 with metabolic syndrome X. Diabetologia. 1997; 40(11):1286-92.
133. Schmidt M I, Duncan B B, Sharrett A R, Lindberg G, Savage P J, Offenbacher S, Azambuja M I, Tracy R P, Heiss G. Markers of inflammation and prediction of diabetes mellitus in adults (Atherosclerosis Risk in Communities study): a cohort study. Lancet. 1999; 353(9165):1649-52.
134. Duncan B B, Schmidt M I, Pankow J S, Ballantyne C M, Couper D, Vigo A, Hoogeveen R, Folsom A R, Heiss G, Atherosclerosis Risk in Communities Study. Low-grade systemic inflammation and the development of type 2 diabetes: the atherosclerosis risk in communities study. Diabetes. 2003; 52(7):1799-805.
135. Duncan B B, Schmidt M I, Chambless L E, Folsom A R, Carpenter M, Heiss G. Fibrinogen, other putative markers of inflammation, and weight gain in middle-aged adults—the ARIC study. Atherosclerosis Risk in Communities. Obes Res. 2000; 8(4):279-86.
136. Pradhan A D, Manson J E, Rifai N, Buring J E, Ridker P M. C-reactive protein, interleukin 6, and risk of developing type 2 diabetes mellitus. JAMA. 2001; 286(3):327-34.
137. Barzilay J I, Abraham L, Heckbert S R, Cushman M, Kuller L H, Resnick H E, Tracy R P. The relation of markers of inflammation to the development of glucose disorders in the elderly: the Cardiovascular Health Study. Diabetes. 2001; 50(10):2384-9.
138. Han T S, Sattar N, Williams K, Gonzalez-Villalpando C, Lean M E, Haffner S M. Prospective study of C-reactive protein in relation to the development of diabetes and metabolic syndrome in the Mexico City Diabetes Study. Diabetes Care. 2002; 25(11):2016-21.
139. Pradhan A D, Cook N R, Buring J E, Manson J E, Ridker P M. C-reactive protein is independently associated with fasting insulin in nondiabetic women. Arterioscler Thromb Vasc Biol. 2003; 23(4):650-5.

EXAMPLE 2

This Example illustrates that, in accordance with the method of the invention, patients managed on the glucose supply side would have fewer cardiovascular events versus those managed on the insulin demand side. In order to test this, the electronic medical records of a group model health maintenance organization were queried to compile a population of patients meeting the following inclusion criteria: (i) T2D; (ii) known date of T2D diagnosis; (iii) ICD-9 or CPT code identification and chart review confirmation of a first major cardiovascular event (myocardial infarction, coronary artery bypass graft, or angioplasty); (iv) 5 years of continuous eligibility, and (v) on antidiabetic therapy at the beginning of the 5-year observation period. These patients were subsequently matched (1:1) to T2D patients meeting the same criteria that had not experienced an event and analyzed for differences in glucose control (HbA$_1$C), the glucose:insulin supply dynamic (SD ratio), and categorical combinations of both parameters.

To help explain the situation where long-term, cardiovascular outcome trials have resulted in counterintuitive outcomes, we have in Example 1 presented data for a pharmacokinetic/pharmacodynamic model that characterizes the effect of conventional antidiabetic therapies on the glucose supply and insulin demand dynamics. To determine if pharmacotherapeutic strategies that favor the glucose supply or insulin demand dynamic are associated with cardiovascular benefit, we retrospectively identified patients with 5-years of eligibility prior to experiencing an initial event, matched them to patients not experiencing an event, and assessed the impact of the glucose supply:insulin demand (SD) ratio in conjunction with measured glucose control (HbA1c).

Methods. The supporting literature and methods used to calculate the SD ratio for each of the antidiabetic agents included in this Example was described in Example 1. In this Example, to test whether patients managed on the glucose supply side would have fewer cardiovascular events versus those managed on the insulin demand side, the electronic medical records of a group model health maintenance organization were queried. From the electronic medical record, de-identified health care claims, medical progress notes, and laboratory data with dates of service spanning Jan. 1, 1997, and Dec. 31, 2008, were reviewed to compile a population of patients meeting the following inclusion criteria: (i) T2D; (ii) known date of T2D diagnosis; (iii) ICD-9 or CPT code identification[5,6] and chart review confirmation of a first major cardiovascular event (myocardial infarction, coronary artery bypass graft, or angioplasty); (iv) 5 years of continuous eligibility, including medical and prescription claims, preceding the initial cardiovascular event; and (v) on antidiabetic therapy at the beginning of the 5-year observation period. From the database of 194,268 patients, an initial query identified 16,007 patients (8.2%) to have ICD-9 code 250 in their medical claims history. Of these, 15,349 (95.9%) were confirmed to have a diagnosis of T2D and 11,751 to have a diagnosis date referenced in their medical history. Within the group of patients with T2D and a known date of diagnosis, 1107 had an initial event, and 50 met the final inclusion parameters of 5 years of continuous medical and prescription claims preceding the event and presence of antidiabetic therapy at the index date. These patients were subsequently matched (1:1) to T2D patients meeting the same criteria that had not experienced an event. Primary baseline matching criteria included age, gender, T2D duration, BMI, and HbA1c. Secondary matching criteria included a composite profile of blood pressure (systolic, diastolic) and cholesterol [low-density lipoprotein, high-density lipoprotein, triglycerides (TG)]. All baseline values were determined, as an average, from the first 6 months of the 5-year observation period. The University at Buffalo's Health Sciences Institutional Review Board previously approved the de-identified database for exempt status; informed consent was not required.

Based on the evidence presented in the aforementioned cardiovascular outcome trials in the T2D population, it was not anticipated that average HbA1c or categorical HbA1c breakpoints would be independently associated with a reduction in cardiovascular outcomes. Similarly, because the SD ratio is a measure of the pharmacologic impact on glucose supply and insulin demand dynamics, it was not anticipated that the average SD ratio or categorical SD ratio breakpoints would be independently associated with a reduction in events. However, we reasoned that combing the optimal SD ratio breakpoint that minimized event rate and the ADA-recommended HbA1c breakpoint (7%) would realize the greatest cardiovascular benefit. Therefore, in addition to evaluating the associations of mean HbA1c, categorical HbA1c ($\geq$7% vs. <7%), mean SD ratio, and categorical SD ratios ($\geq$1, $\geq$1.25, $\geq$1.5) with cardiovascular events, we determined the optimal SD ratio breakpoint that minimized event rate, coupled the breakpoint with the recommended HbA1c threshold (7%), and analyzed the combined parameter for an association with event rate. All statistical assessments of baseline characteristics and cardiovascular outcomes were conducted with the Student's t-test (continuous data) or Chi-square/Fisher's exact test (categorical data).

Results

Application of the Glucose Supply and Insulin Demand Model to Cardiovascular Events. 50 patients with an initial event and known date of occurrence were case matched with noncardiovascular event controls per aforementioned criteria. Baseline characteristics for the event and control patients are presented in Table 2.

TABLE 2

| | Cardiovascular event | Controls | p value |
|---|---|---|---|
| Age (years) | 64.6 ± 10.5 | 64.8 ± 11.0 | .926 |
| Gender (male) | 25 | 25 | 1.00 |
| Duration of T2D (years) | 10.6 ± 5.9 | 10.5 ± 3.6 | .885 |
| Weight | 203.5 ± 50.5 | 203.1 ± 46.5 | .972 |
| BMI (kg/m$^2$) | 32.4 ± 7.1 | 32.5 ± 6.4 | .958 |
| Systolic blood pressure (mmHg) | 142.2 ± 14.3 | 145.0 ± 13.5 | .308 |
| Diastolic blood pressure (mmHg) | 81.1 ± 8.6 | 82.4 ± 9.8 | .466 |
| Low-density lipoprotein (mg/dl) | 114.2 ± 29.9 | 117.5 ± 23.6 | .536 |
| High-density lipoprotein (mg/dl) | 43.0 ± 10.9 | 46.4 ± 11.3 | .129 |
| TG (mg/dl) | 288.8 ± 313.1 | 176.0 ± 81.8 | .017 |
| FPG (mg/dl) | 156.7 ± 49.5 | 163.4 ± 51.9 | .510 |
| HbA1c (%) | 7.7 ± 1.4 | 7.5 ± 1.19 | .484 |
| SD Ratio | 1.1 ± 0.3 | 1.2 ± 0.3 | .051 |
| ACEI/ARB (%) | 32.5 ± 43.6 | 47.6 ± 45.2 | .090 |
| Statin (%) | 29.1 ± 40.3 | 41.3 ± 39.5 | .130 |

ACEI = angiotensin converting enzyme inhibitor,
ARB = angiotensin receptor blocking agent,
BMI = body mass index,
FPG = fasting plasma glucose,
HbA1c = hemoglobin A$_1$C,
SD = glucose supply:insulin demand,
TG = triglycerides Age, gender, duration of T2D, and metabolic characteristics were similar between groups, with the exception of TG that were significantly higher in the cardiovascular event cohort (288.8±313.1 mg/dl versus 176.0±81.8 mg/dl; p=0.017). No significant differences in nondiabetes-related therapies were observed between groups, although more control patients tended to be on angiotensin-converting enzyme inhibitors/angiotensin receptor blocking agents (47.6±45.2% vs. 32.5±43.6%; p=0.090) and also to have higher SD ratio values at baseline (1.2±0.3 vs. 1.1±0.3; p=0.051).

Over the course of the 5-year observation period, there was no significant difference observed for the average HbA1c between event patients and controls (7.5±1.0% vs. 7.3±0.9%; p=0.275, respectively). There was also no difference in event rate between the cohorts when patients were categorized at the HbA1c$\geq$7% breakpoint (72% vs. 64%; p=0.391, respectively). Like HbA1c, the mean SD ratio was not significantly different between the cohorts (1.2±0.3 vs. 1.3±0.3; p=0.205, respectively), and there was also no difference in event rate between the cohorts at the ≧1 (68% vs. 76%; p=0.373, respectively), ≧1.25 (42% vs. 56%; p=0.161, respectively), or ≧1.5 (22% vs. 30%; p=0.362) breakpoints.

Figure 5:
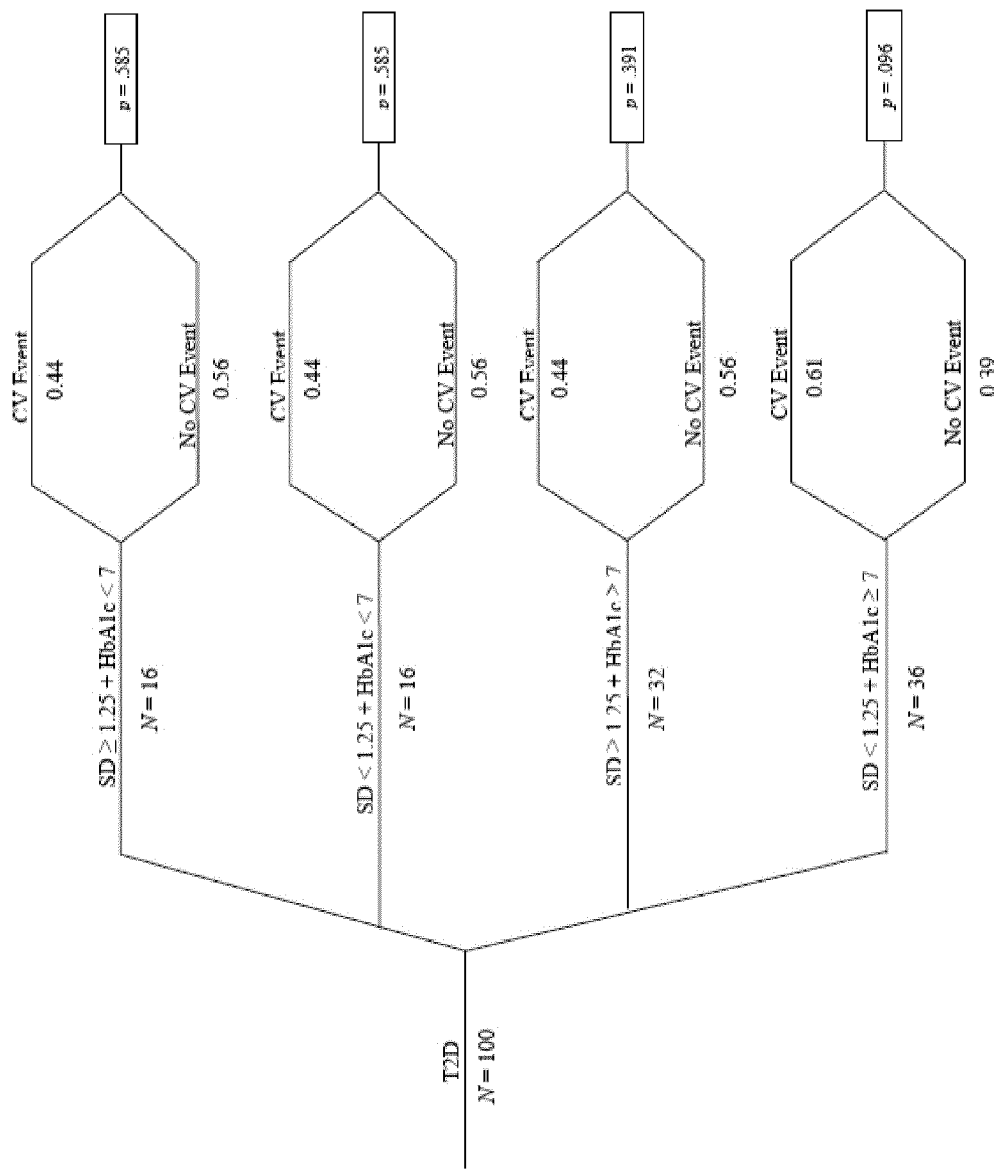
FIG. 5 is a chart illustrating the combined impact of the HbA1c and SD ratio on cardiovascular (CV) event.

We determined that more aggressive HbA1c reduction and higher SD ratio values were not independently associated with a reduction in cardiovascular events. FIG. 5 presents data for the combined impact of the recommended HbA1c breakpoint (<7%) and optimal SD ratio breakpoint (≧1.25) on cardiovascular outcomes. Identical event rates were observed for patients managed to an HbA1c<7% and SD ratio≧1.25, HbA1c<7% and SD ratio<1.25, and HbA1c≧7% and SD ratio≧1.25 (44%). Compared to the remainder of the population, the only group demonstrating a trend toward greater cardiovascular event risk were those managed at higher glucose values and on the insulin demand side of the model (HbA1c≧7% and an SD ratio<1.25; 61% vs. 39%; p=0.096).

As can be seen from the foregoing description, the overwhelming evidence that intensive blood glucose management does not confer a corresponding reduction in macrovascular events requires evaluation of the interventions used to attain the reductions in HbA1c. The impact of pharmacologic intervention has been largely dismissed in the assessment of recent T2D cardiovascular outcome trials.[1-3] Close inspection of therapies utilized during the trials demonstrates a focus on agents that predominantly increase PIE and peripheral glucose disposal. At baseline of the ADVANCE trial, patients in the intensive and standard groups were predominantly on sulfonylurea- (71.8% and 71.1%) and metformin-(61.0% and 60.2%) based regimens with minimal insulin utilization (1.5% and 1.4%). At end of follow-up, sulfonylurea (92.4%) and insulin utilization (40.5%) spiked in the intensive treatment group, while in the standard group, sulfonylurea utilization decreased (58.7%) and insulin use moderately increased (24.1%).[2] Similarly, the ACCORD trial featured greater secretagogue and insulin exposure in those receiving intensive therapy versus standard therapy (86.6% and 73.8% vs. 77.3% and 55.4%, respectively).[1] The VADT determined initial treatment class by BMI, metformin+rosiglitazone when ≧27 kg/m², glimepiride+rosiglitazone when <27 kg/m². Subsequently, the intensive management cohort received maximal doses, while standard therapy received one-half the maximal dose.[3] Notably, before any changes in oral medications were made, insulin was added to patients in the intensive management cohort not achieving a HbA1c<6% and only to standard-therapy patients not achieving a HbA1c<9%. Thus, in summary, by analyzing the relationship between cardiovascular events, blood glucose reduction, and the SD ratio, our invention indicates that for patients managed at higher HbA1c values (≧7%), there may be a protective cardiovascular effect if pharmacologically managed on the glucose supply side (SD ratio≧1.25).

References for Example 2:
1. Action to Control Cardiovascular Risk in Diabetes Study Group, Gerstein H C, Miller M E, Byington R P, Goff D C Jr, Bigger J T, Buse J B, Cushman W C, Genuth S, Ismail-Beigi F, Grimm R H Jr, Probstfield J L, Simons-Morton D G, Friedewald W T. Effects of intensive glucose lowering in type 2 diabetes. N Engl J Med. 2008; 358(24):2545-59.
2. ADVANCE Collaborative Group, Patel A, MacMahon S, Chalmers J, Neal B, Billot L, Woodward M, Marre M, Cooper M, Glasziou P, Grobbee D, Hamet P, Harrap S, Heller S, Liu L, Mancia G, Mogensen C E, Pan C, Poulter N, Rodgers A, Williams B, Bompoint S, de Galan B E, Joshi R, Travert F. Intensive blood glucose control and vascular outcomes in patients with type 2 diabetes. N Engl J Med. 2008; 358(24):2560-72.
3. Duckworth W, Abraira C, Moritz T, Reda D, Emanuele N, Reaven P D, Zieve F J, Marks J, Davis S N, Hayward R, Warren S R, Goldman S, McCarren M, Vitek M E, Henderson W G, Huang G D, VADT Investigators. Glucose control and vascular complications in veterans with type 2 diabetes. N Engl J Med. 2009; 360(2):129-39.
4. Editor to Reference for Parent Paper (Manuscript 1)
5. Newton K M, Wagner E H, Ramsey S D, McCulloch D, Evans R, Sandhu N, Davis C. The use of automated data to identify complications and comorbidities of diabetes: a validation study. J Clin Epidemiol. 1999; 52(3):199-207.
6. Pladevall M, Goff D C, Nichaman M Z, Chan F, Ramsey D, Ortiz C, Labarthe D R. An assessment of the validity of ICD Code 410 to identify hospital admissions for myocardial infarction: The Corpus Christi Heart Project. Int J Epidemiol. 1996; 25(5):948-52.
7. Bays H E, Goldberg R B. The 'forgotten' bile acid sequestrants: is now a good time to remember? Am J Ther. 2007; 14(6):567-80.
8. Stulnig T M, Oppermann U, Steffensen K R, Schuster G U, Gustafsson J A. Liver X receptors downregulate 11beta-hydroxysteroid dehydrogenase type 1 expression and activity. Diabetes. 2002; 51(8):2426-33.
9. Cao G, Liang Y, Broderick C L, Oldham B A, Beyer T P, Schmidt R J, Zhang Y, Stayrook K R, Suen C, Otto K A, Miller A R, Dai J, Foxworthy P, Gao H, Ryan T P, Jiang X C, Burris T P, Eacho P I, Etgen G J. Antidiabetic action of a liver x receptor agonist mediated by inhibition of hepatic gluconeogenesis. J Biol Chem. 2003; 278(2):1131-6.
10. Laffitte B A, Chao L C, Li J, Walczak R, Hummasti S, Joseph S B, Castrillo A, Wilpitz D C, Mangelsdorf D J, Collins J L, Saez E, Tontonoz P. Activation of liver X receptor improves glucose tolerance through coordinate regulation of glucose metabolism in liver and adipose tissue. Proc Natl Acad Sci USA. 2003; 100(9):5419-24.
11. Efanov A M, Sewing S, Bokvist K, Gromada J. Liver X receptor activation stimulates insulin secretion via modulation of glucose and lipid metabolism in pancreatic beta-cells. Diabetes. 2004; 53 Suppl 3:S75-8.
12. Ma K, Saha P K, Chan L, Moore D D. Farnesoid X receptor is essential for normal glucose homeostasis. J Clin Invest. 2006; 116(4):1102-9.
13. Mitro N, Mak P A, Vargas L, Godio C, Hampton E, Molteni V, Kreusch A, Saez E. The nuclear receptor LXR is a glucose sensor. Nature. 2007; 445(7124):219-23.
14. Thomson A B, Keelan M. Feeding rats diets containing cheno- or ursodeoxycholic acid or cholestyramine modifies intestinal uptake of glucose and lipids. Digestion. 1987; 38(3):160-70.
15. Feldman E B, Watt R, Feldman D S. Conjugated dihydroxy bile salt inhibition of glucose influx in rat jejunum in vitro. Am J Dig Dis. 1977; 22(5):415-8.
16. Kogire M, Gomez G, Uchida T, Ishizuka J, Greeley G H Jr, Thompson J C. Chronic effect of oral cholestyramine, a bile salt sequestrant, and exogenous cholecystokinin on insulin release in rats. Pancreas. 1992; 7(1):15-20.
17. Brand S J, Morgan R G. Stimulation of pancreatic secretion and growth in the rat after feeding cholestyramine. Gastroenterology. 1982; 83(4):851-9.
18. Koide M, Okabayashi Y, Otsuki M. Role of endogenous bile on basal and postprandial CCK release in humans. Dig Dis Sci. 1993; 38(7):1284-90.
19. Gomez G, Upp J R Jr, Lluis F, Alexander R W, Poston G J, Greeley G H Jr, Thompson J C. Regulation of the release of cholecystokinin by bile salts in dogs and humans. Gastroenterology. 1988; 94(4):1036-46.
20. Katsuma S, Hirasawa A, Tsujimoto G. Bile acids promote glucagon-like peptide-1 secretion through TGR5 in a murine enteroendocrine cell line STC-1. Biochem Biophys Res Commun. 2005; 329(1):386-90.
21. Inoue Y, Yu A M, Yim S H, Ma X, Krausz K W, Inoue J, Xiang C C, Brownstein M J, Eggertsen G, Björkhem I, Gonzalez F J. Regulation of bile acid biosynthesis by hepatocyte nuclear factor 4alpha. J Lipid Res. 2006; 47(1):215-27.
22. De Fabiani E, Mitro N, Gilardi F, Caruso D, Galli G, Crestani M. Coordinated control of cholesterol catabolism to bile acids and of gluconeogenesis via a novel mechanism of transcription regulation linked to the fasted-to-fed cycle. J Biol Chem. 2003; 278(40):39124-32.
23. Bays H E, Cohen D E. Rationale and design of a prospective clinical trial program to evaluate the glucose-lowering effects of colesevelam HCl in patients with type 2 diabetes mellitus. Curr Med Res Opin. 2007; 23(7):1673-84.
24. Gustafsson B E, Angelin B, Einarsson K, Gustafsson J A. Influence of cholestyramine on synthesis of cholesterol and bile acids in germfree rats. J Lipid Res. 1978; 19(8): 972-7.
25. DeFronzo R A, Okerson T, Viswanathan P, Guan X, Holcombe J H, MacConell L. Effects of exenatide versus sitagliptin on postprandial glucose, insulin and glucagon secretion, gastric emptying, and caloric intake: a randomized, cross-over study. Curr Med Res Opin. 2008; 24(10): 2943-52.
26. Scott K A, Moran T H. The GLP-1 agonist exendin-4 reduces food intake in nonhuman primates through changes in meal size. Am J Physiol Regul Integr Comp Physiol. 2007; 293(3):R983-7.
27. Edwards C M, Stanley S A, Davis R, Brynes A E, Frost G S, Seal L J, Ghatei M A, Bloom S R. Exendin-4 reduces fasting and postprandial glucose and decreases energy intake in healthy volunteers. Am J Physiol Endocrinol Metab. 2001; 281(1):E155-61.
28. Cervera A, Wajcberg E, Triplitt C, Fernandez M, Joya J, Zuo P, DeFronzo R A, Cersosimo E. Different effects of acute vs. chronic exenatide administration on the mechanism of attenuation of post-meal glucose in T2DM. American Diabetes Association 68th Scientific Sessions 2008, Jun. 6-10, 2008, San Francisco, Calif.
29. Cervera A, Wajcberg E, Sriwijitkamol A, Fernandez M, Zuo P, Triplitt C, Musi N, DeFronzo R A, Cersosimo E. Mechanism of action of exenatide to reduce postprandial hyperglycemia in type 2 diabetes. Am J Physiol Endocrinol Metab. 2008; 294(5):E846-52.
30. Kolterman O G, Buse J B, Fineman M S, Gaines E, Heintz S, Bicsak T A, Taylor K, Kim D, Aisporna M, Wang Y, Baron A D. Synthetic exendin-4 (exenatide) significantly reduces postprandial and fasting plasma glucose in subjects with type 2 diabetes. J Clin Endocrinol Metab. 2003; 88(7):3082-9.
31. Raz I, Hanefeld M, Xu L, Caria C, Williams-Herman D, Khatami H, Sitagliptin Study 023 Group. Efficacy and safety of the dipeptidyl peptidase-4 inhibitor sitagliptin as monotherapy in patients with type 2 diabetes mellitus. Diabetologia. 2006; 49(11):2564-71.
32. Chapman I, Parker B, Doran S, Feinle-Bisset C, Wishart J, Strobel S, Wang Y, Burns C, Lush C, Weyer C, Horowitz M. Effect of pramlintide on satiety and food intake in obese subjects and subjects with type 2 diabetes. Diabetologia. 2005; 48(5):838-48.
33. Pullman J, Darsow T, Frias J P. Pramlintide in the management of insulin-using patients with type 2 and type 1 diabetes. Vasc Health Risk Manag. 2006; 2(3):203-12.
34. Hollander P, Maggs D G, Ruggles J A, Fineman M, Shen L, Kolterman O G, Weyer C. Effect of pramlintide on weight in overweight and obese insulin-treated type 2 diabetes patients. Obes Res. 2004; 12(4):661-8.
35. Hollander P, Ratner R, Fineman M, Strobel S, Shen L, Maggs D, Kolterman O, Weyer C. Addition of pramlintide to insulin therapy lowers HbA1c in conjunction with weight loss in patients with type 2 diabetes approaching glycaemic targets. Diabetes Obes Metab. 2003; 5(6):408-14.
36. Hollander P A, Levy P, Fineman M S, Maggs D G, Shen L Z, Strobel S A, Weyer C, Kolterman O G. Pramlintide as an adjunct to insulin therapy improves long-term glycemic and weight control in patients with type 2 diabetes: a 1-year randomized controlled trial. Diabetes Care. 2003; 26(3): 784-90.
37. Ratner R E, Want L L, Fineman M S, Velte M J, Ruggles J A, Gottlieb A, Weyer C, Kolterman O G. Adjunctive therapy with the amylin analogue pramlintide leads to a combined improvement in glycemic and weight control in insulin-treated subjects with type 2 diabetes. Diabetes Technol Ther. 2002; 4(1):51-61.
38. Whitehouse F, Kruger D F, Fineman M, Shen L, Ruggles J A, Maggs D G, Weyer C, Kolterman O G. A randomized study and open-label extension evaluating the long-term efficacy of pramlintide as an adjunct to insulin therapy in type 1 diabetes. Diabetes Care. 2002; 25(4):724-30.
39. Vella A, Lee J S, Camilleri M, Szarka L A, Burton D D, Zinsmeister A R, Rizza R A, Klein P D. Effects of pramlintide, an amylin analogue, on gastric emptying in type 1 and 2 diabetes mellitus. Neurogastroenterol Motil. 2002; 14(2):123-31.
40. Kong M F, King P, Macdonald I A, Stubbs T A, Perkins A C, Blackshaw P E, Moyses C, Tattersall R B. Infusion of pramlintide, a human amylin analogue, delays gastric emptying in men with IDDM. Diabetologia. 1997; 40(1):82-8.
41. Kong M F, Stubbs T A, King P, Macdonald I A, Lambourne J E, Blackshaw P E, Perkins A C, Tattersall R B. The effect of single doses of pramlintide on gastric emptying of two meals in men with IDDM. Diabetologia. 1998; 41(5): 577-83.
42. Kong M F, Macdonald I A, Tattersall R B. Gastric emptying in diabetes. Diabet Med. 1996; 13(2):112-9.
43. Kellmeyer T A, Kesty N C, Wang Y, Frias J P, Fineman M S. Pharmacokinetics of an oral drug (acetaminophen) administered at various times relative to subcutaneous injection of pramlintide in subjects with type 2 diabetes. J Clin Pharmacol. 2007; 47(7):798-805.
44. Fineman M, Weyer C, Maggs D G, Strobel S, Kolterman O G. The human amylin analog, pramlintide, reduces postprandial hyperglucagonemia in patients with type 2 diabetes mellitus. Horm Metab Res. 2002; 34(9):504-8.
45. Fineman M S, Koda J E, Shen L Z, Strobel S A, Maggs D G, Weyer C, Kolterman O G. The human amylin analog, pramlintide, corrects postprandial hyperglucagonemia in patients with type 1 diabetes. Metabolism. 2002; 51(5): 636-41.
46. Nyholm B, Orskov L, Hove K Y, Gravholt C H, Møller N, Alberti K G, Moyses C, Kolterman O, Schmitz O. The amylin analog pramlintide improves glycemic control and reduces postprandial glucagon concentrations in patients with type 1 diabetes mellitus. Metabolism. 1999; 48(7): 935-41.

47. Ceriello A, Lush C W, Darsow T, Piconi L, Corgnali M, Nanayakkara N, Frias J P, Maggs D. Pramlintide reduced markers of oxidative stress in the postprandial period in patients with type 2 diabetes. Diabetes Metab Res Rev. 2008; 24(2):103-8.
48. Orskov L, Nyholm B, Yde Hove K, Gravholt C H, Møller N, Schmitz O. Effects of the amylin analogue pramlintide on hepatic glucagon responses and intermediary metabolism in type 1 diabetic subjects. Diabet Med. 1999; 16(10): 867-74.

EXAMPLE 3

This Example provides a description and illustrative examples of expected results obtained by implementation of the method of the invention under several exemplary scenarios.

Illustrative Case Example: Baseline Patient Presentation: Patient AB is a 5'8, 94.3 kg (body mass index of 31.6 kg/m$^2$), 53 yo male with new onset type 2 diabetes mellitus (T2D). Upon the advice of his physician ten years ago he quit smoking. At present, he is negative for cardiovascular complications of peripheral arterial disease, coronary artery disease, coronary revascularization procedures, myocardial infarction, or ischemic stroke. Clinical evaluation and consultation reveals that his blood pressure is slightly elevated (138/82 mmHg), his diet is high in fat and carbohydrate, and he does not participate in aerobic activities. Laboratory analysis revealed his hemoglobin $A_1C$ to be 7.2%, LDL cholesterol to be 102 mg/dL, HDL cholesterol to be 42 mg/dL, and triglycerides to be 187 mg/dL. His current medication regimen includes only Lisinopril 10 mg daily and Simvastatin 40 mg at bedtime.

Management Scenario 1: Patient AB is given Insulin Glargine at a dose of 47 units (0.5 units/kg/day) to be administered subcutaneously once daily at bedtime. He returns to the clinic 3-months later with no significant change in his cardiovascular history and his blood pressure (136/84 mmHg), body mass index (31.6 kg/m$^2$), dietary habits, and physical activity habits have not significantly changed. His hemoglobin $A_1C$ has declined to 6.7%, while his LDL cholesterol (104 mg/dL), HDL cholesterol (43 mg/dL), and triglycerides (168 mg/dL) have not significantly changed. His medication regimen now includes the Insulin Glargine 47 units daily, Lisinopril 10 mg daily, and Simvastatin 40 mg at bedtime.

Management Scenario 2: Patient AB is given Metformin at an oral dose of 1,000 mg twice daily. He returns to the clinic 3-months later with no significant change in his cardiovascular history and his blood pressure (136/84 mmHg), body mass index (31.6 kg/m$^2$), dietary habits, and physical activity habits have not significantly changed. His hemoglobin $A_1C$ has declined to 6.7%, while his LDL cholesterol (104 mg/dL), HDL cholesterol (43 mg/dL), and triglycerides (168 mg/dL) have not significantly changed. His medication regimen now includes the Metformin 1,000 mg twice daily, Lisinopril 10 mg daily, and Simvastatin 40 mg at bedtime.

Management Scenario 3: Patient AB elects to undergo Roux-en-Y gastric bypass. He returns to the clinic 3-months later with a hemoglobin $A_1C$ reduction to 6.7% without significant change in his cardiovascular history, blood pressure (136/84 mmHg), LDL cholesterol (104 mg/dL), HDL cholesterol (43 mg/dL), triglycerides (168 mg/dL) or medications. He has lost 22.7 kg reducing his body mass index to 24.0 kg/m$^2$. Because of the surgery he can only eat low carb, low fat meals or he gets extremely nauseous and he has yet to start exercising. Supply/Demand Calculations for Antidiabetic Therapeutic Interventions:

Supply/Demand (SD) Calculation for Metformin 2000 mg Daily (Table 3):

TABLE 3

| Category | Score | Supply (1 + (CE + HGU + GNG + IR)) | Demand (1 + (PIE + PGU)) | Ratio (Supply/Demand) |
|---|---|---|---|---|
| CE | 0.15 | 2.28 | 1.04 | 2.20 |
| HGU | 0.40 | | | |
| HGI | 0.35 | | | |
| IR | 0.38 | | | |
| PIE | −0.10 | | | |
| PGU | 0.14 | | | |

Supply/Demand Calculation for Glyburide 10 mg Daily (Table 4):

TABLE 4

| Category | Score | Supply (1 + (CE + HGU + GNG + IR)) | Demand (1 + (PIE + PGU)) | Ratio (Supply/Demand) |
|---|---|---|---|---|
| CE | 0.00 | 1.21 | 1.57 | 0.77 |
| HGU | 0.14 | | | |
| HGI | 0.07 | | | |
| IR | 0.00 | | | |
| PIE | 0.21 | | | |
| PGU | 0.36 | | | |

Supply/Demand Calculation for Pioglitazone 45 mg Daily (Table 5):

TABLE 5

| Category | Score | Supply (1 + (CE + HGU + GNG + IR)) | Demand (1 + (PIE + PGU)) | Ratio (Supply/Demand) |
|---|---|---|---|---|
| CE | 0.00 | 1.97 | 1.49 | 1.32 |
| HGU | 0.40 | | | |
| HGI | 0.21 | | | |
| IR | 0.35 | | | |
| PIE | −0.10 | | | |
| PGU | 0.59 | | | |

Supply/Demand Calculation for Insulin Glargine 0.5 U/kg Daily (Table 6):

TABLE 6

| Category | Score | Supply (1 + (CE + HGU + GNG + IR)) | Demand (1 + (PIE + PGU)) | Ratio (Supply/Demand) |
|---|---|---|---|---|
| CE | 0.00 | 1.34 | 1.72 | 0.78 |
| HGU | 0.24 | | | |
| HGI | 0.10 | | | |
| IR | 0.00 | | | |
| PIE | 0.30 | | | |
| PGU | 0.42 | | | |

Supply/Demand Calculation for Insulin Glargine 1.0 U/kg Daily (Table 7):

TABLE 7

| Category | Score | Supply (1 + (CE + HGU + GNG + IR)) | Demand (1 + (PIE + PGU)) | Ratio (Supply/Demand) |
|---|---|---|---|---|
| CE | 0.00 | 1.68 | 2.44 | 0.69 |
| HGU | 0.48 | | | |
| HGI | 0.20 | | | |
| IR | 0.00 | | | |
| PIE | 0.60 | | | |
| PGU | 0.84 | | | |

Supply/Demand Calculation for Metformin 2000 mg daily + Insulin Glargine 0.5 U/kg Daily (Table 8):

TABLE 8

| Category | Score | Supply (1 + (CE + HGU + GNG + IR)) | Demand (1 + (PIE + PGU)) | Ratio (Supply/Demand) |
|---|---|---|---|---|
| CE | 0.15 | 2.62 | 1.76 | 1.49 |
| HGU | 0.64 | | | |
| HGI | 0.45 | | | |
| IR | 0.38 | | | |
| PIE | 0.20 | | | |
| PGU | 0.56 | | | |

Supply/Demand Calculation for pH Encapsulated Glucose, 3.0 grams/day Between Meals (Table 9):

TABLE 9

| Category | Score | Supply (1 + (CE + HGU + GNG + IR)) | Demand (1 + (PIE + PGU)) | Ratio (Supply/Demand) |
|---|---|---|---|---|
| CE | 0.45 | 2.85 | 1.00 | 2.85 |
| HGU | 0.75 | | | |
| HGI | 0.45 | | | |
| IR | 0.20 | | | |
| PIE | −0.15 | | | |
| PGU | 0.15 | | | |

Supply/Demand Calculation for Roux-en-Y Gastric Bypass (Table 10):

TABLE 10

| Category | Score | Supply (1 + (CE + HGU + GNG + IR)) | Demand (1 + (PIE + PGU)) | Ratio (Supply/Demand) |
|---|---|---|---|---|
| CE | 0.75 | 3.80 | 0.80 | 4.75 |
| HGU | 0.85 | | | |
| HGI | 0.75 | | | |
| IR | 0.45 | | | |
| PIE | −0.35 | | | |
| PGU | 0.15 | | | |

A Risk scoring table for Predicting Macrovascular Events (Myocardial Infarction, Stroke, CV-related Death) in Patients Afflicted with Type 2 Diabetes Mellitus (the Look-Up table) is presented in FIG. 6. Baseline Scoring for Patient AB is presented in FIG. 7. The risk scoring table for Management Scenario 1 (Insulin Glargine 47 units to be administered subcutaneously once daily at bedtime) is presented in FIG. 8. The risk scoring table for Management Scenario 2 (Metformin 1,000 mg orally twice daily) is presented in FIG. 9. The risk scoring table for Management Scenario 3 (Roux-en-Y Gastric Bypass) is presented in FIG. 10.

Case Summary and Rationale for Supply Side Management of T2D:

Pharmacotherapeutic Management Strategies (Scenario 1 and Scenario 2)

In the above case summary three management strategies are presented for example patient AB. In the first management example, utilizing Insulin Glargine at a dose of 47 units daily (0.5 units/kg/day) was able to significantly reduce the hemoglobin $A_1C$, but was not able to diminish the macrovascular event score because of an increase in the Supply/Demand score with all other variables being held constant. Conversely, the Metformin regimen was able to reduce the macrovascular event score at the same level of hemoglobin $A_1C$ lowering because the Supply/Demand score was also reduced while holding all other variables constant. In this particular patient case, there was no occurrence of worsening dietary habits, weight gain, and/or hypoglycemic events that are common with anti-diabetic agents such as Insulin and Secretagogues, but not Amylinomimetics, Alpha-glucosidase Inhibitors, Bile-acid Sequestrants, Dopamine Agonists, DPP-IV inhibitors, GLP-1 agonists, Metformin, and Thiazolidinediones. Therefore, because worsening dietary habits, weight gain, and/or hypoglycemic events would elevate the macrovascular event risk score, it is possible that macrovascular detriment may be seen when administering Insulin and Secretagogue therapy despite an improvement in the hemoglobin $A_1C$. Moreover, this Supply side model of macrovascular disease progression in the T2D patient provides both an explanation for why neutral/poor outcomes were observed in large-scale randomized controlled trials that more aggressively reduced hemoglobin $A_1C$ and also a therapeutic algorithm to maximize the benefit of antidiabetic therapies that lower blood glucose.

Intestinal Glucose Regulation Management Strategies (Scenario 3)

In the remaining management strategy, Roux-en-Y gastric bypass was performed resulting in improved dietary habits and a significant reduction in weight within a 3-month period. Holding all other variables constant (age, gender, T2D duration, smoking history, vascular disease history, blood pressure, hypoglycemia, physical activity, LDL-cholesterol, HDL cholesterol, triglycerides, concomitant cardiovascular therapies) and at the same degree of $HbA_1C$ lowering, the Roux-en-Y gastric bypass procedure was able to most effectively reduce the macrovascular event score because the dietary score (from carbohydrate and fat reductions), body mass index score (from significant weight loss), and the Supply/Demand score (from surgical induced physiologic effects, primarily on the intestine) were all significantly reduced. In this model of macrovascular disease progression in the T2D patient, the Roux-en-Y gastric bypass procedure (and also extending to other bariatric malabsorptive and restrictive procedures) is a non-pharmacologic example that demonstrates macrovascular benefit beyond glucose lowering that is consistent with the teachings of the Supply side management algorithm. The use of pH encapsulated glucose would be expected to yield results similar, but of slightly lesser magnitude to Roux-en-Y gastric bypass because of similar physiologic effects at the level of the intestine. Therefore, in patients that are either unable or unwilling to undergo bariatric surgical intervention, pH encapsulated glucose would serve as a next best treatment approach because it would be expected to demonstrate superior dietary alterations, weight loss, and Supply/Demand dynamics in comparison to all other pharmacologic approaches, but in particular those that would decrease the Supply/Demand ratio and increase the likelihood for continuing poor dietary habits as well as hypoglycemia, weight gain, and physical inactivity (i.e. insulin and secretagogues).

We claim:

1. A method for lowering cardiovascular risk for a Type 2 diabetic patient who is being treated with at least one anti-diabetes drug, the method comprising:

obtaining from the Type 2 diabetic a first biological sample at a first time point, and from the first biological sample a) determining one or more physiological parameters and a ratio of a Glucose Supply Index (S) to an Insulin Demand Index (D) by determining (S) for the Type 2 diabetic patient calculated as follows:

1+[aggregate of carbohydrate exposure (CE)+hepatic glucose uptake (HGU)+hepatic gluconeogenesis (GNG) and+insulin resistance (IR) for the at least one drug], and (D) calculated as follows:

1+[aggregate of peripheral glucose uptake (PGU)+ peripheral insulin exposure (PIE) for the at least one drug];

to obtain an S/D ratio for the at least one drug in the Type 2 diabetic patient;

b) assign a first cardiovascular risk score for the Type 2 diabetic patient by summing values for one or more physiological parameters in look-up table provided in FIG. 6 and the S/D ratio;

c) obtaining a second biological sample at a second time point from the Type 2 diabetic and repeat steps a) and b) for the second biological sample to obtain a second cardiovascular risk score;

d) comparing the first cardiovascular risk score to the second cardiovascular risk score and determining from the comparing that the Type 2 diabetes patient is at greater cardiovascular risk, and administering to the Type 2 diabetes patient a drug, wherein the drug is pH-encapsulated glucose, wherein glucose is released at or above pH of 7.0.

2. The method of claim 1, wherein the pH encapsulated glucose is administered in combination with an additional agent selected from the group consisting of anti-diabetes drugs, hormones, GLP-1, lipids, proteins, amino-acids, other sugars or carbohydrates, and combinations thereof.

3. The method of claim 2, wherein the ratio of S to D for a combination of the drugs is determined using a microprocessor.

4. The method of claim 2, wherein the ratio of S to D for a combination of the drugs is determined using a programmable spreadsheet.

* * * * *